(12) United States Patent
Rousso et al.

(10) Patent No.: US 8,111,886 B2
(45) Date of Patent: Feb. 7, 2012

(54) RECONSTRUCTION STABILIZER AND ACTIVE VISION

(75) Inventors: Benny Rousso, Rishon-LeZion (IL); Eli Dichterman, Haifa (IL); Omer Ziv, Rechovot (IL); Shlomo Ben-Haim, London (GB)

(73) Assignee: Spectrum Dynamics LLC, Orangeburg, NY (US)

( * ) Notice: Subject to any disclaimer, the term of this patent is extended or adjusted under 35 U.S.C. 154(b) by 615 days.

(21) Appl. No.: 11/988,926

(22) PCT Filed: Jul. 19, 2006

(86) PCT No.: PCT/IL2006/000840
§ 371 (c)(1),
(2), (4) Date: Feb. 5, 2009

(87) PCT Pub. No.: WO2007/010537
PCT Pub. Date: Jan. 25, 2007

(65) Prior Publication Data
US 2009/0190807 A1    Jul. 30, 2009

Related U.S. Application Data

(63) Continuation-in-part of application No. PCT/IL2006/000562, filed on May 11, 2006, and a continuation-in-part of application No. PCT/IL2006/000059, filed on Jan. 15, 2006, and a continuation-in-part of application No. PCT/IL2005/001215, filed on Nov. 16, 2005, and a continuation-in-part of application No. PCT/IL2005/001173, filed on Nov. 9, 2005.

(60) Provisional application No. 60/816,970, filed on Jun. 28, 2006, provisional application No. 60/800,846, filed on May 17, 2006, provisional application No. 60/800,845, filed on May 17, 2006, provisional application No. 60/799,688, filed on May 11, 2006, provisional application No. 60/763,458, filed on Jan. 31, 2006, provisional application No. 60/750,597, filed on Dec. 15, 2005, provisional application No. 60/750,334, filed on Dec. 15, 2005, provisional application No. 60/750,287, filed on Dec. 13, 2005, provisional application No. 60/741,440, filed on Dec. 2, 2005, provisional application No. 60/720,652, filed on Sep. 27, 2005, provisional application No. 60/720,541, filed on Sep. 27, 2005, provisional application No. 60/720,034, filed on Sep. 26, 2005, provisional application No. 60/702,979, filed on Jul. 28, 2005, provisional application No. 60/700,753, filed on Jul. 20, 2005, provisional application No. 60/700,752, filed on Jul. 20, 2005, provisional application No. 60/700,318, filed on Jul. 19, 2005, provisional application No. 60/700,299, filed on Jul. 19, 2005, provisional application No. 60/700,317, filed on Jul. 19, 2005.

(30) Foreign Application Priority Data

Oct. 10, 2005 (IL) .......................................... 171346
Nov. 27, 2005 (IL) .......................................... 172349

(51) Int. Cl.
*G06K 9/00* (2006.01)

(52) U.S. Cl. ........................................ 382/128; 382/254

(58) Field of Classification Search .................. 382/128, 382/130, 160, 254; 378/4, 7
See application file for complete search history.

(56) References Cited

U.S. PATENT DOCUMENTS 2,776,377 A    1/1957    Anger
(Continued)

FOREIGN PATENT DOCUMENTS

DE    1516429    12/1969
(Continued)

OTHER PUBLICATIONS

Communication Pursuant to Article 94(3) EPC Dated Mar. 2, 2011 From the European Patent Office Re.: Application No. 06756259.5.
(Continued)

*Primary Examiner* — Louis Arana

(57) ABSTRACT

A method for stabilizing the reconstruction of an imaged volume is presented. The method includes the steps of performing an analysis of the reliability of reconstruction of a radioactive-emission density distribution of the volume from radiation detected over a specified set of views, and defining modifications to the reconstruction process and/or data collection process to improve the reliability of reconstruction, in accordance with the analysis.

20 Claims, 30 Drawing Sheets

U.S. PATENT DOCUMENTS

| | | |
|---|---|---|
| 3,340,866 A | 9/1967 | Nöller |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 4,015,592 A | 4/1977 | Bradley-Moore |
| 4,278,077 A | 7/1981 | Mizumoto |
| 4,302,675 A | 11/1981 | Wake et al. |
| 4,364,377 A | 12/1982 | Smith |
| 4,521,688 A | 6/1985 | Yin |
| H12 H | 1/1986 | Bennett et al. |
| 4,595,014 A | 6/1986 | Barrett et al. |
| 4,674,107 A | 6/1987 | Urban et al. |
| 4,689,041 A | 8/1987 | Corday et al. |
| 4,689,621 A | 8/1987 | Kleinberg |
| 4,731,536 A | 3/1988 | Rische et al. |
| 4,773,430 A | 9/1988 | Porath |
| 4,828,841 A | 5/1989 | Porter et al. |
| 4,844,067 A | 7/1989 | Ikada et al. |
| 4,844,076 A | 7/1989 | Lesho et al. |
| 4,893,013 A | 1/1990 | Denen et al. |
| 4,928,250 A | 5/1990 | Greenberg et al. |
| 4,929,832 A | 5/1990 | Ledley |
| 4,951,653 A | 8/1990 | Fry et al. |
| 4,959,547 A | 9/1990 | Carroll et al. |
| 4,995,396 A | 2/1991 | Inaba et al. |
| 5,014,708 A | 5/1991 | Hayashi et al. |
| 5,032,729 A | 7/1991 | Charpak |
| 5,033,998 A | 7/1991 | Corday et al. |
| 5,070,878 A | 12/1991 | Denen |
| 5,088,492 A | 2/1992 | Takayama et al. |
| 5,119,818 A | 6/1992 | Carroll et al. |
| 5,151,598 A | 9/1992 | Denen |
| 5,170,055 A | 12/1992 | Carroll et al. |
| 5,170,789 A | 12/1992 | Narayan et al. |
| 5,243,988 A | 9/1993 | Sieben et al. |
| 5,246,005 A | 9/1993 | Carroll et al. |
| 5,249,124 A | 9/1993 | DeVito |
| 5,279,607 A | 1/1994 | Schentag et al. |
| 5,299,253 A | 3/1994 | Wessels |
| 5,307,808 A | 5/1994 | Dumoulin et al. |
| 5,349,190 A | 9/1994 | Hines et al. |
| 5,383,456 A | 1/1995 | Arnold et al. |
| 5,386,446 A | 1/1995 | Fujimoto et al. |
| 5,395,366 A | 3/1995 | D'Andrea et al. |
| 5,399,868 A | 3/1995 | Jones et al. |
| 5,415,181 A | 5/1995 | Hofgrefe et al. |
| 5,441,050 A | 8/1995 | Thurston et al. |
| 5,448,073 A | 9/1995 | Jeanguillaume |
| 5,475,219 A | 12/1995 | Olson |
| 5,484,384 A | 1/1996 | Fearnot |
| 5,489,782 A | 2/1996 | Wernikoff |
| 5,493,595 A | 2/1996 | Schoolman |
| 5,519,221 A | 5/1996 | Weinberg |
| 5,572,999 A | 11/1996 | Funda et al. |
| 5,579,766 A | 12/1996 | Gray |
| 5,604,531 A | 2/1997 | Iddan et al. |
| 5,617,858 A | 4/1997 | Taverna et al. |
| 5,635,717 A | 6/1997 | Popescu |
| 5,657,759 A | 8/1997 | Essen-Moller |
| 5,672,877 A | 9/1997 | Liebig et al. |
| 5,682,888 A | 11/1997 | Olson et al. |
| 5,690,691 A | 11/1997 | Chen et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,744,805 A | 4/1998 | Raylman et al. |
| 5,784,432 A | 7/1998 | Kurtz et al. |
| 5,803,914 A | 9/1998 | Ryals et al. |
| 5,811,814 A | 9/1998 | Leone et al. |
| 5,821,541 A | 10/1998 | Tümer |
| 5,833,603 A | 11/1998 | Kovacs et al. |
| 5,838,009 A | 11/1998 | Plummer et al. |
| 5,842,977 A | 12/1998 | Lesho et al. |
| 5,846,513 A | 12/1998 | Carroll et al. |
| 5,857,463 A | 1/1999 | Thurston et al. |
| 5,871,013 A | 2/1999 | Wainer et al. |
| 5,880,475 A | 3/1999 | Oka et al. |
| 5,891,030 A | 4/1999 | Johnson et al. |
| 5,900,533 A | 5/1999 | Chou |
| 5,916,167 A | 6/1999 | Kramer et al. |
| 5,928,150 A | 7/1999 | Call |
| 5,932,879 A | 8/1999 | Raylman et al. |
| 5,939,724 A | 8/1999 | Eisen et al. |
| 5,961,457 A | 10/1999 | Raylman et al. |
| 5,984,860 A | 11/1999 | Shan |
| 5,987,350 A | 11/1999 | Thurston |
| 5,993,378 A | 11/1999 | Lemelson |
| 6,002,480 A | 12/1999 | Izatt et al. |
| 6,072,177 A | 6/2000 | McCroskey et al. |
| 6,076,009 A | 6/2000 | Raylman et al. |
| 6,082,366 A | 7/2000 | Andra et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,147,353 A | 11/2000 | Gagnon et al. |
| 6,160,398 A * | 12/2000 | Walsh ........................... 324/309 |
| 6,173,201 B1 | 1/2001 | Front |
| 6,205,347 B1 | 3/2001 | Morgan et al. |
| 6,212,423 B1 | 4/2001 | Krakovitz |
| 6,226,350 B1 | 5/2001 | Hsieh |
| 6,233,304 B1 | 5/2001 | Hu et al. |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,242,743 B1 | 6/2001 | DeVito et al. |
| 6,246,901 B1 | 6/2001 | Benaron |
| 6,252,924 B1 | 6/2001 | Davantes et al. |
| 6,261,562 B1 | 7/2001 | Xu et al. |
| 6,263,229 B1 | 7/2001 | Atalar et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,310,968 B1 | 10/2001 | Hawkins et al. |
| 6,324,418 B1 | 11/2001 | Crowley et al. |
| 6,339,652 B1 | 1/2002 | Hawkins et al. |
| 6,346,706 B1 | 2/2002 | Rogers et al. |
| 6,368,331 B1 | 4/2002 | Front et al. |
| 6,381,349 B1 | 4/2002 | Zeng et al. |
| 6,392,235 B1 | 5/2002 | Barrett et al. |
| 6,407,391 B1 | 6/2002 | Mastrippolito et al. |
| 6,415,046 B1 | 7/2002 | Kerut, Sr. |
| 6,420,711 B2 | 7/2002 | Tuemer |
| 6,426,917 B1 | 7/2002 | Tabanou et al. |
| 6,429,431 B1 | 8/2002 | Wilk |
| 6,431,175 B1 | 8/2002 | Penner et al. |
| 6,438,401 B1 | 8/2002 | Cheng et al. |
| 6,453,199 B1 | 9/2002 | Kobozev |
| 6,459,925 B1 | 10/2002 | Nields et al. |
| 6,480,732 B1 | 11/2002 | Tanaka et al. |
| 6,484,051 B1 | 11/2002 | Daniel |
| 6,490,476 B1 | 12/2002 | Townsend et al. |
| 6,510,336 B1 | 1/2003 | Daghighian et al. |
| 6,516,213 B1 | 2/2003 | Nevo |
| 6,525,320 B1 | 2/2003 | Juni |
| 6,525,321 B2 | 2/2003 | Juni |
| 6,549,646 B1 | 4/2003 | Yeh et al. |
| 6,560,354 B1 | 5/2003 | Maurer et al. |
| 6,567,687 B2 | 5/2003 | Front et al. |
| 6,584,348 B2 | 6/2003 | Glukhovsky |
| 6,587,710 B1 | 7/2003 | Wainer |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,628,983 B1 | 9/2003 | Gagnon |
| 6,628,984 B2 | 9/2003 | Weinberg |
| 6,632,216 B2 | 10/2003 | Houzego et al. |
| 6,633,658 B1 | 10/2003 | Dabney et al. |

| | | |
|---|---|---|
| 6,638,752 B2 | 10/2003 | Contag et al. |
| 6,643,538 B1 | 11/2003 | Majewski et al. |
| 6,662,036 B2 | 12/2003 | Cosman |
| 6,680,750 B1 | 1/2004 | Tournier et al. |
| 6,697,660 B1 | 2/2004 | Robinson |
| 6,728,583 B2 | 4/2004 | Hallett |
| 6,748,259 B1 | 6/2004 | Benaron et al. |
| 6,766,048 B1 | 7/2004 | Launay et al. |
| 6,771,802 B1 | 8/2004 | Patt et al. |
| 6,776,977 B2 | 8/2004 | Liu |
| 6,943,355 B2 | 9/2005 | Shwartz et al. |
| 6,963,770 B2 | 11/2005 | Scarantino et al. |
| 7,043,063 B1 | 5/2006 | Noble et al. |
| 7,103,204 B1 | 9/2006 | Celler et al. |
| 7,142,634 B2 | 11/2006 | Engler et al. |
| 7,176,466 B2 | 2/2007 | Rousso et al. |
| 7,187,790 B2 | 3/2007 | Sabol et al. |
| 7,327,822 B2 * | 2/2008 | Sauer et al. ............... 378/4 |
| 7,359,535 B2 | 4/2008 | Salla et al. |
| 7,468,513 B2 | 12/2008 | Charron et al. |
| 7,490,085 B2 | 2/2009 | Walker et al. |
| 7,570,732 B2 * | 8/2009 | Stanton et al. ............... 378/7 |
| 7,620,444 B2 | 11/2009 | Le et al. |
| 7,680,240 B2 * | 3/2010 | Manjeshwar et al. ......... 378/4 |
| 7,705,316 B2 * | 4/2010 | Rousso et al. ......... 250/370.09 |
| 7,968,851 B2 * | 6/2011 | Rousso et al. ......... 250/370.09 |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0103431 A1 | 8/2002 | Toker et al. |
| 2002/0148970 A1 | 10/2002 | Wong et al. |
| 2002/0168317 A1 | 11/2002 | Daighighian et al. |
| 2002/0183645 A1 | 12/2002 | Nachaliel |
| 2002/0188197 A1 | 12/2002 | Bishop et al. |
| 2003/0001837 A1 | 1/2003 | Baumberg |
| 2003/0013966 A1 | 1/2003 | Barnes et al. |
| 2003/0063787 A1 | 4/2003 | Natanzon et al. |
| 2003/0081716 A1 | 5/2003 | Tumer |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215124 A1 | 11/2003 | Li |
| 2003/0216631 A1 | 11/2003 | Bloch et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0054248 A1 | 3/2004 | Kimchy et al. |
| 2004/0054278 A1 | 3/2004 | Kimchy et al. |
| 2004/0081623 A1 | 4/2004 | Eriksen et al. |
| 2004/0086437 A1 | 5/2004 | Jackson et al. |
| 2004/0101176 A1 | 5/2004 | Mendonca et al. |
| 2004/0116807 A1 | 6/2004 | Amrami et al. |
| 2004/0122311 A1 | 6/2004 | Cosman |
| 2004/0138557 A1 | 7/2004 | Le et al. |
| 2004/0153128 A1 | 8/2004 | Suresh et al. |
| 2004/0171924 A1 | 9/2004 | Mire et al. |
| 2004/0184644 A1 | 9/2004 | Leichter et al. |
| 2004/0195512 A1 | 10/2004 | Crosetto |
| 2004/0204646 A1 | 10/2004 | Nagler et al. |
| 2004/0251419 A1 | 12/2004 | Nelson et al. |
| 2005/0020915 A1 | 1/2005 | Bellardinelli et al. |
| 2005/0033157 A1 | 2/2005 | Klein et al. |
| 2005/0055174 A1 | 3/2005 | David et al. |
| 2005/0205792 A1 | 9/2005 | Rousso et al. |
| 2005/0211909 A1 | 9/2005 | Smith |
| 2005/0215889 A1 | 9/2005 | Patterson, II |
| 2005/0253073 A1 | 11/2005 | Joram et al. |
| 2005/0266074 A1 | 12/2005 | Zilberstein et al. |
| 2006/0074290 A1 | 4/2006 | Chen et al. |
| 2006/0160157 A1 | 7/2006 | Zuckerman |
| 2006/0237652 A1 | 10/2006 | Kimchy et al. |
| 2006/0257012 A1 | 11/2006 | Kaufman et al. |
| 2007/0156047 A1 | 7/2007 | Nagler et al. |
| 2007/0166227 A1 | 7/2007 | Liu et al. |
| 2007/0194241 A1 | 8/2007 | Rousso et al. |
| 2008/0033291 A1 | 2/2008 | Rousso et al. |
| 2008/0042067 A1 | 2/2008 | Rousso et al. |
| 2008/0128626 A1 | 6/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260637 A1 | 10/2008 | Dickman |
| 2008/0277591 A1 | 11/2008 | Shahar et al. |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0201291 A1 | 8/2009 | Ziv et al. |
| 2010/0245354 A1 | 9/2010 | Rousso et al. |

FOREIGN PATENT DOCUMENTS

| | | |
|---|---|---|
| DE | 19814199 | 10/1999 |
| DE | 19815362 | 10/1999 |
| EP | 0543626 | 5/1993 |
| EP | 0697193 | 2/1996 |
| EP | 0887661 | 12/1998 |
| GB | 2031142 | 4/1980 |
| JP | 6-109848 | 4/1994 |
| JP | 06-109848 | 4/1994 |
| WO | WO 92/00402 | 1/1992 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/31522 | 6/2000 |
| WO | WO 01/89384 | 11/2001 |
| WO | WO 02/16965 | 2/2002 |
| WO | WO 02/058531 | 8/2002 |
| WO | WO 2004/042546 | 5/2004 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Notice of Allowance Dated Nov. 15, 2010 From the US Patent and Trademark Office Re. U.S. Appl. No. 10/616,301.

Notice of Non-Compliant Amendment Dated Feb. 14, 2011 From the US Patent and Trademark Office Re.: U.S. Appl. No. 10/616,307.

Response Dated Feb. 10, 2011 to Notice of Allowance of Nov. 15, 2010 From the US Patent and Trademark Office Re. U.S. Appl. No. 10/616,301.

Mettler et al. "Legal Requirements and Radiation Safety", Essentials of Nuclear Medicine Imaging, 2nd Ed., Chap.13: 323-331, 1985.

Notice of Allowance Dated Feb. 23, 2011 From the US Patent and Trademark Office Re.: U.S. Appl. No. 11/980,690.

Official Action Dated Mar. 15, 2011 From the US Patent and Trademark Office Re.: U.S. Appl. No. 10/343,792.

Response Dated Mar. 24, 2011 to Official Action of Dec. 8, 2010 From the US Patent and Trademark Office Re.: U.S. Appl. No. 09/641,973.

Official Action Dated May 23, 2011 From the US Patent and Trademark Office Re. U.S. Appl. No. 11/667,793.

Official Action Dated May 23, 2011 From the US Patent and Trademark Office Re. U.S. Appl. No. 10/616,307.

Official Action Dated May 23, 2011 From the US Patent and Trademark Office Re.: U.S. Appl. No. 11/980,690.

Chengazi et al. "Imaging Prostate Cancer With Technetium-99m-7E11-C5.3 (CYT-.351)", Journal of Nuclear Medicine, 38: 675-682, 1997.

McJilton et al. "Protein Kinase Cε Interacts With Bax and Promotes Survival of Human Prostate Cancer Cells", Oncogene, 22; 7958-7968, 2003.

Xu et al. "Quantitative Expression Profile of Androgen-Regulated Genes in Prostate Cancer Cells and Identification of Prostate-Specific Genes", International Journal of Cancer, 92: 322-328, 2001.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Interview Summary Dated May 31, 2011 From the US Patent and Trademark Office Re. U.S. Appl. No. 10/616,301.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Official Action Dated Jun. 28, 2011 From the US Patent and Trademark Office Re. U.S. Appl. No. 11/628,074.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated Jul. 15, 2009 From the US Patent and Trademark Office Re.: U.S. Appl. No. 10/616,301.
Official Action Dated Jul. 20, 2009 From the US Patent and Trademark Office Re.: U.S. Appl. No. 11/980,617.

Bloch et al. "Application of Computerized Tomography to Radiation Therapy and Surgical Planning", Proceedings of the IEEE, 71(3): 351-355, Mar. 1983.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report dated Sep. 12, 2002 From the International Searching Authority of the Patent Cooperation Treaty Re: Application No. PCT/IL02/00057.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Dec. 16, 2008 From the US Patent and Trademark Office Re.: U.S. Appl. No. 10/343,792.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S Appl. No. 10/240,239.
Official Action Dated Apr. 29, 2009 From the US Patent and Trademark Office Re.: U.S. Appl. No. 11/980,690.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.

Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Oct. 31, 2007 to Official Action of Jul. 12, 2007 From the US Patent and Trademark Office Re.: U.S. Appl. No. 10/616,301.
Response Dated Apr. 7, 2009 to Official Action of Oct. 7, 2008 From the US Patent and Trademark Office Re.: U.S. Appl. No. 10/616,301.
Response to the International Search Report and the Written Opinion of Oct. 10, 2006 From the International Searching Authority Re.: Application No. PCT/IL06/00059.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Response dated Sep. 1, 2010 to Official Action of Aug. 3, 2010 From the US Patent and Trademark Office Re.: U.S. Appl. No. 11/980,690.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
International Search Report Dated Oct. 10, 2006 From the International Searching Authority of the Patent Cooperation Treaty Re.: Application No. PCT/IL06/00059.
International Search Report Dated May 24, 2007 From the International Searching Authority of the Patent Cooperation Treaty Re.: Application No. PCT/IL05/00575.
Notice of Appeal Dated Nov. 16, 2009 to Official Action of Jul. 15, 2009 From the US Patent and Trademark Office Re.: U.S. Appl. No. 10/616,301.
Office Action Dated Dec. 2, 2007 From the Israeli Patent Office Re.: Application No. 158442.
Official Action Dated Jun. 1, 2006 From the US Patent and Trademark Office Re.: U.S. Appl. No. 10/686,536.
Official Action Dated May 3, 2007 From the US Patent and Trademark Office Re.: U.S. Appl. No. 10/240,239.
Official Action Dated Sep. 5, 2002 From the US Patent and Trademark Office Re.: U.S. Appl. No. 12/084,559.
Official Action Dated Jan. 7, 2009 From the US Patent and Trademark Office Re.: U.S. Appl. No. 10/616,307.
Official Action Dated Oct. 7, 2008 From the US Patent and Trademark Office Re.: U.S. Appl. No. 10/616,301.
Official Action Dated Apr. 8, 2010 From the US Patent and Trademark Office Re.: U.S. Appl. No. 11/980,690.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Official Action Dated Sep. 15, 2009 From the US Patent and Trademark Office Re.: U.S. Appl. No. 10/616,307.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Response to the International Search Report and the Written Opinion of Oct. 10, 2006 From the International Searching Authority Re.: Appliction No. PCT/IL06/00059.
Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, Co1. 2, § 2.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Hassan et al. "A Radiotelemetry Pill for the Measurement of Ionising Radiation Using a Mercuric Iodide Detector", Physics in Medicine and Biology, 23(2): 302-308, 1978.
Jeanguillaume et al. "The Computer Aided Collimation Gamma Camera Project (CACAO) on the Way to Improve SPECT Images", RSNA 2000 Infosystem, 87th Scientific Assembly and Annual Meeting, Chicago, Illinois, 2000.
Kinahan et al. "Attenuation Correction for a Combined 3D PET/CT Scanner", Medical Physics, 25(10): 2046-2053, Oct. 1998.
Lavallée et al. "Building a Hybrid Patient's Model for Augmented Reality in Surgery: A Registration Problem", Computing in Biological Medicine, 25(2): 149-164, 1995.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, Col. 1, Last §.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.

Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Official Action Dated Mar. 19, 2010 From the US Patent and Trademark Office Re.: U.S. Appl. No. 10/240,239.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3)EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "Simultaneous Reconstruction and Motion Estimation for Gated Cardiac ECT", IEEE Transactions on Nuclear Science, XP011077797, 49(5):2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Official Action Dated Apr. 9, 2010 From the US Patent and Trademark Office Re.: U.S. Appl. No. 11/798,017.
Response Dated Mar. 3, 2011 to Notice of Non-Compliant Amendment of Feb. 14, 2011 From the US Patent and Trademark Office Re.: U.S. Appl. No. 10/616,307.
Notice of Allowance Dated May 05, 2011 From the US Patent and Trademark Office Re.: U.S. Appl. No. 10/240,239.
Notice of Allowance Dated Jun. 23, 2011 From the US Patent and Trademark Office Re.: U.S. Appl. No. 10/616,301.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response Dated Jul. 8, 2010 to Communication Pursuant to Article 94(3) EPC of Mar. 8, 2010 From the European Patent Office Re.: Application No. 06832278.3.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.

Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9):2789-2795, Sep. 2004.
Communication Pursuant to Article 93(3) EPC Dated Mar. 8, 2010 From the European Patent Office Re.: Application No. 06832278.3.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hassan et al. "A Radiotelemetry Pill for the Measurement of Ionising Radiation Using a Mercuric Iodide Detector", Phys. Med. Biol., 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.
Kojima et al. "Quantitative Planar Imaging Method for Measurement of Renal Activity by Using a Conjugate-Emission Image and Transmission Data", Medical Physics, 27(3): 608-615, 2000. p. 608.
Lavallée et al. "Building a Hybrid Patient's Model for Augmented Reality in Surgery: A Registration Problem", Computing in Biological Medicine, 25(2): 149-164, 1995. p. 149-150.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Mori et al. "Overexpression of Matrix Metalloproteinase-7mRNA in Human Colon Carcinomas", Cancer, 75: 1516-1519, 1995.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Piperno et al. "Breast Cancer Screening by Impedance Measurements", Frontiers Med. Biol. Engng., 2(2): 11-17, 1990.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedance Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Zhang et al. "An Innovative High Efficiency and High Resolution Probe for Prostate Imaging", The Journal of Nuclear Medicine, 68: 18, 2000. Abstract.
Official Action Dated Jan. 31, 2011 From the US Patent and Trademark Office Re. U.S. Appl. No. 11/667,793.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent. Cooperation Treaty Re.: Application No. PCT/IL06/00840.
international Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.

International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Response Dated Mar. 8, 2011 to Official Action of Dec. 8, 2010 From the US Patent and Trademark Office Re.: U.S. Appl. No. 11/980,690.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Jan. 27, 2011 to Official Action of Nov. 1, 2010 From the US Patent and Trademark Office Re.: U.S. Appl. No. 12/728,383.
Chengazi et al. "Imaging Prostate Cancer With Technetium-99m-7E11-05.3 (CYT-351)", Journal of Nuclear Medicine, 38: 675-682, 1997.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
McJilton et al. "Protein Kinase C? Interacts With Bax and Promotes Survival of Human Prostate Cancer Cells", Oncogene, 22; 7958-7968, 2003.
Response Dated Aug. 25, 2010 to Official Action of Jul. 27, 2010 From the US Patent and Trademark Office Re.: U.S. Appl. No. 10/616,307.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.

Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Sep. 13, 2011 From the US Patent and Trademark Office Re. U.S. Appl. No. 11/976,852.
Ellestad "Stress Testing: Principles and Practice", XP008143015, 5th Edition, p. 432. Jan. 1, 2003.
Gilland et al. "Long Focal Lenth, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction". Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Communication Pursuant to Article 94(3) EPC Dated Nov. 18, 2011 From the European Patent Office Re. Application No. 05803689.8.

Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Response Dated Nov. 14, 2011 to Official Action of Jul. 12, 2011 From the US Patent and Trademark Office Re.: U.S. Appl. No. 09/641,973.
Response Dated Nov. 14, 2011 to Official Action of Sep. 12, 2011 From the US Patent and Trademark Office Re. U.S. Appl. No. 12/087,150.
Response Dated Nov. 23, 2011 to Official Action of May 23, 2011 Front the Its Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Oct. 24, 2011 to Official Action of May 23, 2011 From the US Patent and Trademark Office Re. U.S. Appl. No. 11/667,793.
Response Dated Nov. 28, 2011 to Official Action of Jun. 28, 2011 From the US Patent and Trademark Office Re. U.S. Appl. No. 11/628,074.
Restriction Official Action Dated Nov. 8, 2011 From the US Patent and Trademark Office Re. U.S. Appl. No. 12/309,479.
Restriction Official Action Dated Nov. 15, 2011 From the US Patent and Trademark Office Re. U.S. Appl. No. 11/980,683.
Supplemental Notice of Allowability Dated Oct. 24, 2011 From the US Patent and Trademark Office Re.: U.S. Appl. No. 11/607,075.

\* cited by examiner

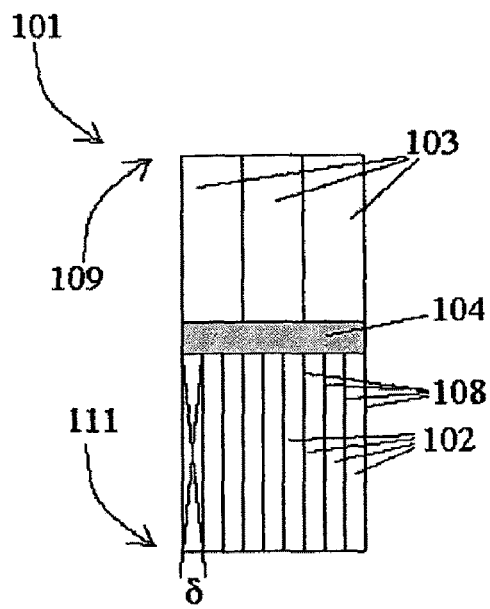
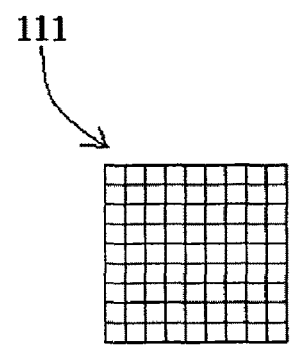
Figure 1e                    Figure 1f
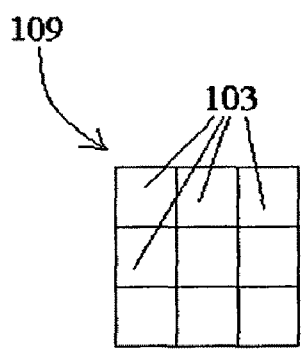
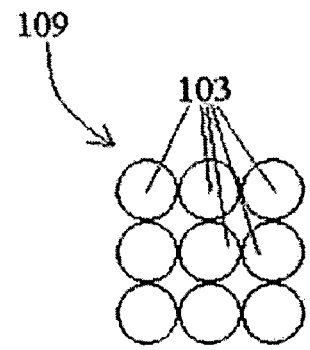
Figure 1g                    Figure 1h

US 8,111,886 B2

RECONSTRUCTION STABILIZER AND ACTIVE VISION

RELATED APPLICATIONS

This application is a National Phase of PCT Patent Application No. PCT/IL2006/000840 having International Filing Date of Jul. 19, 2006, which claims the benefit of the following U.S. Provisional Patent Applications: 60/816,970 filed on Jun. 28, 2006, 60/800,846 filed on May 17, 2006, 60/800,845 filed on May 17, 2006, 60/799,688 filed on May 11, 2006, 60/763,458 filed on Jan. 31, 2006, 60/750,597 filed on Dec. 15, 2005, 60/750,334 filed on Dec. 15, 2005, 60/750,287 filed on Dec. 13, 2005, 60/741,440 filed on Dec. 2, 2005, 60/720,652 filed on Sep. 27, 2005, 60/720,541 filed on Sep. 27, 2005, 60/720,034 filed on Sep. 26, 2005, 60/702,979 filed on Jul. 28, 2005, 60/700,753 filed on Jul. 20, 2005, 60/700,752 filed on Jul. 20, 2005, 60/700,318 filed on Jul. 19, 2005, 60/700,299 filed on Jul. 19, 2005 and 60/700,317 filed on Jul. 19, 2005.

PCT Patent Application No. PCT/IL2006/000840 is also a Continuation-in-Part of the following PCT Patent Applications: PCT/IL2006/000562 filed on May 11, 2006, PCT/IL2006/000059 filed on Jan. 15, 2006, PCT/IL2005/001215 filed on Nov. 16, 2005 and PCT/IL2005/001173 filed on Nov. 9, 2005.

PCT Patent Application No. PCT/IL2006/000840 claims the benefit of Israel Patent Applications: 172349 filed on Nov. 27, 2005 and 171346 filed on Oct. 10, 2005.

The contents of the above Applications are all incorporated herein by reference.

FIELD AND BACKGROUND OF THE INVENTION

The present invention relates to radioactive-emission measurements of a volume. More particularly, the present invention relates to the accurate reconstruction of the volume, based on measurements from non-uniform views of a volume, and on the dynamic selection of views during the data acquisition process. Of particular interest is view selection for medical imaging and/or in conjunction with medical instruments, such as guided minimally invasive surgical instruments.

Radionuclide imaging is one of the most important applications of radioactivity in medicine. Its purpose is to obtain a distribution image of a radioactively labeled substance, e.g., a radiopharmaceutical, within the body following administration thereof to a patient. Radioactive-emission imaging relies on the fact that in general, pathologies, such as malignant tumors, malfunctioning organs, and inflammations, display a level of activity different from that of healthy tissue. Thus, radiopharmaceuticals, which circulate in the blood stream, are picked up by the active pathologies to a different extent than by the surrounding healthy tissue; in consequence, the pathologies are operative as radioactive-emission sources and may be detected by radioactive-emission imaging. It will be appreciated that the pathology may appear as a concentrated source of high radiation, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

Thus radiopharmaceuticals may be used for identifying active pathologies as well as dead tissue.

In the discussion that follows, the term body structure is intended to include organs, portions of organs, a part of the body, and a whole body. The term organ target is intended to include pathological features within organs. These pathological features may be expressed, by radioactive-emission imaging, as any one of the following:

i. hot regions, of a radioactive emission intensity higher than the background level;
ii. regions of low-level radioactive emission intensity, which is nonetheless above the background level; and
iii cold regions, of a radioactive emission intensity, lower than the background level.

Examples of radiopharmaceuticals include monoclonal antibodies or other agents, e.g., fibrinogen or fluorodeoxyglucose, tagged with a radioactive isotope, e.g., $^{99M}$technetium, $^{67}$gallium, $^{201}$thallium, $^{111}$indium, $^{123}$iodine, $^{125}$iodine and $^{18}$fluorine, which may be administered orally or intravenously. The radiopharmaceuticals are designed to concentrate in the area of a tumor, and the uptake of such radiopharmaceuticals in the active part of a tumor, or other pathologies such as an inflammation, is higher and more rapid than in the tissue that neighbors the tumor. Thereafter, a radiation-emission-measuring-probe, which may be configured for extracorporeal or intracorporeal use, is employed for locating the position of the active area. Another application is the detection of blood clots with radiopharmaceuticals such as ACUTECT from Nycomed Amersham for the detection of newly formed thrombosis in veins, or clots in arteries of the heart or brain, in an emergency or operating room. Yet other applications include radioimaging of myocardial infarct using agents such as radioactive anti-myosin antibodies, radioimaging specific cell types using radioactively tagged molecules (also known as molecular imaging), etc.

The usual preferred emission for such applications is that of gamma rays, which emission is in the energy range of approximately 11-511 KeV. Beta radiation and positrons may also be detected.

Radioactive-emission imaging is performed with a radioactive-emission-measuring detector, such as a room temperature, solid-state CdZnTe (CZT) detector, which is among the more promising that are currently available. It may be configured as a single-pixel or a multi-pixel detector. Alternatively, another solid-state detector such as CdTe, HgI, Si, Ge, or the like, or a combination of a scintillation detector (such as NaI(Tl), LSO, GSO, CsI, CaF, or the like) and a photomultiplier, or another detector as known, may be used.

1a-1i schematically illustrate detecting units 102 and detecting blocks 101 of various geometries and constructions, and radioactive-emission-measuring probes associated with them.

FIG. 1a schematically illustrates a detecting unit 102, formed as a single-pixel detector 104, for example, a room-temperature solid-state CdZnTe (CZT) detector, having a diameter D and a thickness $\tau_d$. Both the detector diameter D, or a diameter equivalent in the case of a non-circular detector, and the detector thickness $\tau_d$ affect the detecting efficiency. The detector diameter determines the surface area on which radioactive emission impinges; the greater the surface area, the greater the efficiency. The detector thickness affects the stopping power of the detector. High energy gamma rays may go through a thin detector, and the probability of their detection increases with detector thickness. By itself, a single-pixel detector cannot generate an image; rather, all counts are distributed over the surface area of the detector.

FIG. 1b schematically illustrates the detecting unit 102 with a collimator 108, formed as a single cell of a diameter D, a length L, and a septa thickness $\tau$, attached to the detector 104. The collimator 108 may be, for example, of lead, tungsten or another material which substantially blocks gamma and beta rays.

The collimator's geometry, and specifically, the ratio of D/L, provides the detecting unit 102 with a collection angle δ analogous to a viewing angle of an optical camera. The collection angle δ limits the radioactive-emission detection to substantially only that radioactive emission, which impinges on the detector 104 after passing through a "corridor" of the collimator 108 (although in practice, some high-energy gamma rays may penetrate the collimator's walls).

FIG. 1c schematically illustrates a block 101 of the detecting units 102, with the collimator 108, formed as a multi-cell collimator, of a cell diameter D. The collection angle δ is defined for each of the detecting units 102 in the block, and each of the detecting units 102 forms a pixel in the block 101.

FIG. 1d schematically illustrates a radioactive-emission-measuring probe 100 which comprises several detecting units 102, of different geometries and different collection angles δ, within a housing 107.

FIGS. 1e-1i schematically illustrate the block 101, formed as a combination of a scintillation detector (such as NaI(Tl), LSO, GSO, CsI, CaF, or the like), a collimator grid, and photomultipliers.

As seen in FIG. 1e, the block 101, having proximal and distal ends 109 and 111, respectively, vis a vis an operator (not shown), is formed of the scintillation detector 104, of a single pixel, and the collimators 108, to create the detecting units 102. A plurality of photomultipliers 103 is associated with the single pixel scintillation detector 104, and with proper algorithms, as known, their output can provide a two dimensional image of the scintillations in the single pixel scintillation detector 104. In essence, this is an Anger camera, as known.

The distal view 111 of the collimator grid is seen in FIG. 1f.

Two optional proximal views 109 of the photomultipliers 103 are seen in FIGS. 1g and 1h, as a square grid arrangement, and as an arrangement of tubes.

An Anger camera 117, of the block 101 in the housing 107 is seen in FIG. 1i.

In each of the cases of FIGS. 1a-1i, the geometry of the collimator 108 determines the collection angle δ, wherein with no collimator, the collection angle δ, is essentially a solid angle of 4π steradians. Thus, the collimator's geometry affects both the detection efficiency and the image resolution, which are defined as follows:

i. The detection efficiency is the ratio of measured radiation to emitted radiation; and
ii. The image resolution is the capability of making distinguishable closely adjacent radioactive-emission organ targets, or the capability to accurately determine the size and shape of individual radioactive-emission organ targets.

Naturally, it is desired to optimize both the detection efficiency and the image resolution. Yet, they are inversely related to each other. The detection efficiency increases with increasing collimator's collection angle, and the image resolution decreases with increasing collimator's collection angle. For example, when the ratio of D/L is ½, the collection angle δ is substantially 2.5 steradians, so the cell views incident radiation within the confinement of about a 2.5-steradian sector. However, when the ratio of D/L is 1/12, the collection angle δ is substantially 0.31 steradians, so the cell views incident radiation within the confinement of about a 0.31-steradian sector.

Once the emission data is obtained, the data is processed to reconstruct the intensity distribution within the measured volume. The reconstruction process is generally complex, due to the large quantity of data which must be processed in order to obtain an accurate reconstruction. The following statistical model may be used to perform reconstruction.

We assume an intensity distribution, I, defined over an input space U, where U comprises a set of basic elements (e.g., pixels in two dimensional spaces, voxels in three dimensional spaces), and I(u) is the intensity of a given basic element u∈U. A detecting unit positioned on a radiation-emission-measuring-probe takes a series of measurements $y = (y_i)_{i=1}^T$ from different positions and orientations around the volume U. The geometrical and physical properties of the detecting unit, together with its position and orientation in a given measurement i, determine the detection probability $\phi_i(u)$ of a photon emitted from location u. Thus the effective intensity of location u as viewed by the detecting unit during measurement i is $\phi_i(u)I(u)$.

The random count $X_i(u)$ of photons that are emitted from location u and detected in measurement i is modeled by a Poisson process with mean $\phi_i(u)I(u)$. The total count of photons detected in measurement i is thus:

$$y_i \sim \text{Poisson}(\Sigma_{u \in U} \phi_i(u) I(u)) \quad (1a)$$

or in matrix notation:

$$y = \text{Poisson}(\Phi I) \quad (1b)$$

where y is the vector of measurements $y_i$, $\Phi$ is a matrix of detection probabilities over measurements i and voxels u, and I is a vector of intensity per voxel u. The reconstruction problem is to reconstruct the intensities I from the measurements y.

The 2-D Radon transform is a mathematical relationship which may be used to reconstruct the emission intensities of volume U when the set of measurements $(y_t)_{t=1}^T$ is unconstrained. The Radon transform is not statistical and does not take into account the Poissonian nature of the counts. In addition, it models the views as line projections. The Radon transform maps the spatial domain (x,y) to the Radon domain (p,φ). For a fixed projection angle, the Radon transform is simply a projection of the object. A technique known in the art as filtered back-projection (FBP) uses a back-projection operator and the inverse of the Radon transform to reconstruct the intensity distribution in volume U from measurements $(y_t)_{t=1}^T$.

The basic, idealized problem solved by the FBP approach is to reconstruct an image from its Radon transform. The Radon transform, when properly defined, has a well-defined inverse. However, in order to invert the transform one needs measured data spanning 180°. In many medical imaging situations, the positioning of the detecting unit relative to the emitting object is constrained, so that complete measured data is not available. Reconstruction based on filtered back-projection is therefore of limited use for medical imaging. Maximum likelihood (ML) and Maximum A Posteriori (MAP) estimation methods, which address the statistical nature of the counts, have been found to provide better image reconstructions than FBP.

Limited-angle tomography is a reconstruction technique in the related art which reconstructs an image from projections acquired over a limited range of angular directions. The success of the reconstruction process depends upon the extent of the angular range acquired compared with the angular range of the missing projections. Any reconstruction from a limited range of projections potentially results in spatial distortions (artifacts) in the image. Limited angle techniques can be applied for both the Radon transform and the statistical models, but better results are generally achieved within the statistical framework. While it is known that the severity of the artifacts increases with the increasing angular range of the missing projections, limited-angle tomography does not provide information on which projections should be used in order to most effectively reconstruct the image.

Maximum likelihood (ML) estimation is a widely used method in the related art for reconstructing an image from a constrained set of measurements. A parameterization of the generative model described above is obtained by assigning an intensity I(u) to every voxel in U. The likelihood of the observed data y=(y$_t$)$_t$, given the set of parameters I={I(u): u∈U} is:

$$L(y \mid I) = \ln P(y \mid I) \quad (2)$$

$$= \ln \prod_t P(y_t \mid I)$$

$$= \sum_t \ln P\left(\sum_u x_t(u) \mid I\right)$$

$$= \sum_t \ln Poisson\left(y_t \mid \sum_u \phi_t(u)I(u)\right)$$

$$= \sum_t \left\{ -\sum_u \phi_t(u)I(u) + y_t \ln \sum_u \phi_t(u)I(u) - \ln(y_t!) \right\}$$

Note that the lower and upper bound of an indexing variable (such as voxels u and time index t) are omitted in the following description, when they are clear from the context.

There is currently no analytic way to solve Eqn. 2 for the maximum of the likelihood function. However, optimization methods that find local maxima of the likelihood are known. One such method is the Expectation-Maximization (EM) process. In EM estimation, there is no guarantee that the sequence converges to a maximum likelihood estimator. For multimodal distributions, this means that an EM algorithm will converge to a local maximum (or saddle point) of the observed data likelihood function, depending on starting values.

Since the data generated by the model is only partially observable by our measurements, a basic ingredient of the Expectation-Maximization formalism is to define a set of random variables that completely define the data generated by the model. In the current case, since Y$_t$=Σ$_u$X$_t$(u), the set of variables {X$_u$(t):u∈U; t=1, . . . , T} is such a set; the generated data is x=(x$_t$)$_t$, where x$_t$=(x$_t$(u))$_u$, and the observed data y is completely determined by x. The main tool in the EM formalism is the complete data likelihood:

$$\ln P(x \mid I) = \ln \prod_t P(x_t \mid I) \quad (3)$$

$$= \sum_t \ln \prod_u Poisson(x_t(u) \mid \phi_t(u)I(u))$$

$$= \sum_t \sum_u \{-\phi_t(u)I(u) + x_t(u)\ln(\phi_t(u)I(u)) + \ln(x_t(u)!)\}$$

Since the likelihood depends on the complete data, which is only partially observable, we take its expectation with respect to the space of the unobserved data, given the current set of hypothesized parameters (i.e. the current estimator). The result is a function Q(I|I') which assigns likelihood to sets I of model parameters, given the current set I', and given the observed data y:

$$Q(I \mid I') = E[\ln P(x \mid I) \mid y; I'] \quad (4)$$

$$= \sum_t \sum_u \{-\phi_t(u)I(u) + E[x_t(u) \mid y_t; I']\ln(\phi_t(u)I(u)) + C\}$$

where C is a term which is independent of the intensities I. The function Q(I|I') is maximized by the following new estimates:

$$I(u) = \frac{1}{\sum_t \phi_t(u)} \sum_t E[x_t(u) \mid y_t; I']; \forall u \in U. \quad (5)$$

The expectation in Eqn. 5 is obtained as follows:

$$P_{X_t(u)}(x_t(u) \mid y_t; I') = \frac{P_{Y_t}(y_t \mid x_t(u); I') P_{X_t(u)}(x_t(u) \mid I')}{P_{Y_t}(y_t \mid I')} \quad (6)$$

$$= \frac{Poisson\left(y_t - x_t(u) \mid \sum_{v \neq u} \phi_t(v)I'(v)\right) Poisson(x_t(u) \mid \phi_t(u)I'(u))}{Poisson\left(y_t \mid \sum_v \phi_t(v)I(v)\right)}$$

$$= Binomial\left(x_t(u) \mid \frac{\phi_t(u)I'(u)}{\sum_v \phi_t(v)I'(v)}; y_t\right)$$

It follows that $$E[x_t(u) \mid y_t; I'] = y_t \frac{\phi_t(u)I'(u)}{\sum_v \phi_t(v)I'(v)},$$

and hence the EM iteration is:

$$I(u) = \frac{1}{\sum_t \phi_t(u)} \sum_t y_t \frac{\phi_t(u)I'(u)}{\sum_v \phi_t(v)I'(v)} \quad (7)$$

It is provable that each EM iteration improves the likelihood. Thus, given a random starting estimator, the EM algorithm iterates the above improvement step until it converges to a local maximum of the likelihood. Several random starts increase the chance of finding a globally good estimator.

It is usually desired to maximize the expected posterior probability (given a proper prior) rather than the expected likelihood. In that case we assume a prior probability on the intensities P(I)=Π$_u$P(I(u)). A proper conjugate prior for the Poisson distribution is the Gamma distribution:

$$P(I(u)) = Gamma(I(u) \mid \alpha_u; \beta_u) = \frac{\beta_u^{\alpha_u+1}}{\Gamma(\alpha_u+1)} I(u)^{\alpha_u} e^{-\beta_u I(u)} \quad (8)$$

Now the maximization is done on Q(I|I')=E[lnP(x|I)p(I)|y; I']. Plugging the Gamma prior into Q, and solving for I(u), we get the following EM iteration for the maximum posterior estimation:

$$I(u) = \frac{\alpha_u + \sum_t E[x_t(u) \mid y_t; I']}{\beta_u + \sum \phi_t(u)} \quad (9)$$

$$= \frac{1}{\beta_u + \sum_t \phi_t(u)} \left[ \alpha_u + \sum_t y_t \frac{\phi_t(u) I'(u)}{\sum_v \phi_t(v) I'(v)} \right] \quad (10)$$

The EM update step can be formulated in matrix notation as follows. Let $\Phi$ be the matrix of the projections $[\phi_t(u)]_{t,u}$, and let I, I', y, $\alpha$ and $\beta$ be represented as column vectors. Eqn. 10 can be written in vector and matrix notations as:

$$I = \frac{\alpha + I' \cdot \left( \Phi^T \frac{y}{\Phi I'} \right)}{\beta + \Phi^T 1} \quad (11)$$

where the explicit multiplication and division denote element-wise operations, and where 1 is a vector (of the appropriate length) consisting solely of 1's.

Limited computational resources (i.e., when the entire projection matrix $\Phi$ cannot be kept in memory) may require breaking the update computation according to a partition of $\Phi$ into a set of sub-matrices ($\Phi_i$). In that case the intensities can be updated gradually (using only one sub-matrix at each step) according to the following computation:

$$I = \frac{\alpha + I' \cdot \sum_i \Phi_i^T \frac{y_i}{\Phi_i I'}}{\beta + \sum_i \Phi_i^T 1} \quad (12)$$

where $y_i$ is the vector of observations that are obtained using the views of $\Phi_i$.

In the context of image reconstruction from a constrained set of views, the utility of the reconstruction algorithms described above is limited. Many estimation algorithms, including EM and the Radon transform, require measurements from a complete set of views surrounding the imaged object. Although algorithms for EM with missing views have been developed, these algorithms are based on equally spaced views surrounding the imaged object, of which a number of views are not available. These algorithms do not provide a generalized solution for an unconstrained set of views, which may not be equally spaced or available for all directions surrounding the object.

Singular value decomposition (SVD) is a known technique for factorizing a rectangular real or complex matrix, with applications in signal processing and statistics. SVD may be considered a generalization of Eigenvalue decomposition to m*n matrices, whereas Eigenvalue decomposition is applicable only to square matrices.

SVD states that given the m-by-n matrix M whose entries are either from the field of real numbers or the field of complex numbers, there exists a factorization of the form:

$$M = UDV^T \quad (13)$$

where U is an m-by-m unitary matrix, D is m-by-n with nonnegative numbers on the diagonal and zeros off the diagonal, and $V^T$, the conjugate transpose of V, is an n-by-n unitary matrix. The elements along the diagonal of D are denoted the singular values. Such a factorization is called a singular-value decomposition of M. A common convention is to order the singular values $D_{i,i}$ in non-increasing fashion, so that the diagonal matrix D is uniquely determined by M.

The condition number of a matrix is defined as the ratio of the matrix's largest singular value to its smallest singular value. In numerical analysis, the condition number associated with a problem is a measure of that problem's amenability to digital computation. A problem with a low condition number is said to be well-conditioned, while a problem with a high condition number is said to be ill-conditioned. For example, the condition number associated with the linear equation x=My gives a bound on how accurate the solution y will be after approximate solution.

SVD may be employed for the solution of linear inverse problems. The inverse problem for a set of linear equations, x=My, is to calculate vector y from a known x and M. Using SVD, with M=UDV*, the problem may be restated as x=UDV*y. If D is an invertible matrix, y is obtained as:

$$y = V D^{-1} U^T x \quad (14)$$

where U and $V^t$ are unitary matrices, and D is a diagonal matrix containing the singular values of M. Since U and $V^t$ are easily transposable, a solution to Eqn. 13 is obtainable only if D is invertible. As D is a diagonal matrix of singular values $e_1$ to $e_n$ (where $e_k$ denotes the k-th singular value $D_{k,k}$), $D^{-1}$ is a diagonal matrix of the reciprocals of the singular values. That is:

$$D^{-1} = \begin{bmatrix} e_1^{-1} & & & \\ & e_2^{-1} & & \\ & & \ldots & \\ & & & e_n^{-1} \end{bmatrix} \quad (15)$$

If the dimension of y is larger than the dimension of x, y cannot be determined directly but rather can only be estimated, which is often performed by an iterative procedure. If the condition number of D is very large, the multiplicative factors $e_i^{-1}$ will vary greatly, thus multiplying any measurement or calculation errors based on individual or linear combinations of elements of y, and decreasing the likelihood of convergence of the iterative estimation procedure.

Truncated SVD is a known technique for reducing sensitivity to inaccuracies or noise when solving a set of linear equations. In truncated SVD, the constraints associated with the smaller singular values are eliminated from the estimation. In terms of the inverse problem of Eqn. 14, this is accomplished for the i-th singular value by setting $e_i^{-1}$ equal to zero in matrix $D^{-1}$. Thus the lower valued singular values no longer affect the estimation process.

In order to achieve a reconstructed image which is adequate for medical diagnostic and treatment purposes, a reliable, high-resolution image of the tested object (i.e. body structure) must be obtained. Currently, reliable reconstruction algorithms are available only for complete data sets, which provide coverage of the entire volume. Such data is generally not available during medical imaging. Additionally, when high-resolution detecting units are used, their efficiency is relatively low, and the detecting units must remain at each position for a relatively long time in order to achieve a high probability of detection. Since during medical testing, measurements are generally performed at many locations as the detecting unit is moved relative to the observed body structure, the testing procedure generally requires a long time and is physically and emotionally difficult for the patient. Additionally, reconstruction is based upon a large quantity of data, and is a lengthy and computationally complex process.

There is thus a widely recognized need for, and it would be highly advantageous to have, an apparatus, system and method devoid of the above limitations.

SUMMARY OF THE INVENTION

According to a first aspect of the present invention there is provided a method for stabilizing the reconstruction of an imaged volume. The method includes the steps of performing an analysis of the reliability of reconstruction of a radioactive-emission density distribution of the volume from radiation detected over a specified set of views, and defining modifications to the reconstruction process and/or data collection process to improve the reliability of reconstruction, in accordance with the analysis.

According to a second aspect of the present invention there is provided a reconstruction stabilizer, for improving the reliability of reconstruction of an imaged volume, according to a preferred embodiment of the present invention. The reconstruction stabilizer includes a reliability analyzer for performing an analysis of the reliability of reconstruction of a radioactive-emission density distribution of the volume from radiation detected over a specified set of views, and a modifier associated with the reliability analyzer, for defining modifications to at least one of a reconstruction process and a data collection process to improve the reliability of reconstruction, in accordance with the analysis.

According to a third aspect of the present invention there is provided a system for generating a three-dimensional image of volume, according to a preferred embodiment of the present invention. The system includes a radiological imaging camera comprising a plurality of detectors configured for independent movement during data acquisition, and configured for detecting radiation emitted from the volume thereby to provide radiation data, a reconstructor, configured for performing an analysis of the radiation data so as to reconstruct a three-dimensional image of the volume, and a reconstruction stabilizer associated with the camera and the reconstructor. The reconstruction stabilizer includes a reliability analyzer for performing an analysis of the reliability of reconstruction of a radioactive-emission density distribution of the volume from radiation detected over a specified set of views, and a modifier associated with the reliability analyzer, for defining modifications to at least one of a reconstruction process and a data collection process to improve the reliability of reconstruction, in accordance with the analysis, and for providing the modifications to at least one of the camera and the reconstructor.

According to a fourth aspect of the present invention there is provided a method of radioactive-emission measurements of a body structure, according to a preferred embodiment of the present invention. The method includes the steps of performing radioactive-emission measurements of the body structure, at a predetermined set of views, analyzing the radioactive-emission measurements, and dynamically defining further views for measurements, based on the analyzing.

According to a fifth aspect of the present invention there is provided a measurement unit for performing radioactive-emission measurements of a body structure, according to a preferred embodiment of the present invention. The measurement unit includes a probe for performing the radioactive-emission measurements of the body structure, where the probe is controllable to perform the measurements at a predetermined set of views, an analysis unit for analyzing the radioactive-emission measurements, and a view definer for dynamically defining further views for measurements, based on the analyzing.

The present invention successfully addresses the shortcomings of the presently known configurations by providing methods for stabilizing the reconstruction of an imaged volume and of performing radioactive-emission measurements of a body structure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-1i show detecting units and blocks of various geometries and constructions and radioactive-emission-measuring probes, associated with them.

DESCRIPTION OF THE PREFERRED EMBODIMENTS

Figure 1A:
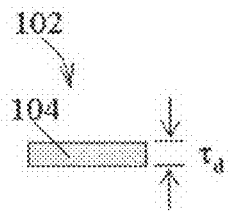
Figure 1B:
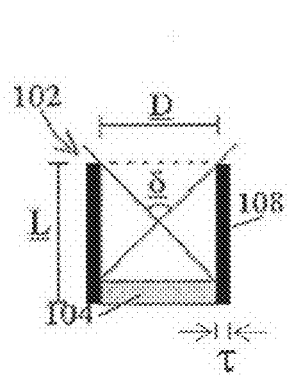
Figure 1C:
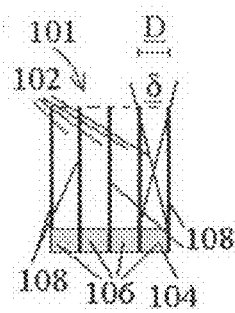
Figure 1D:
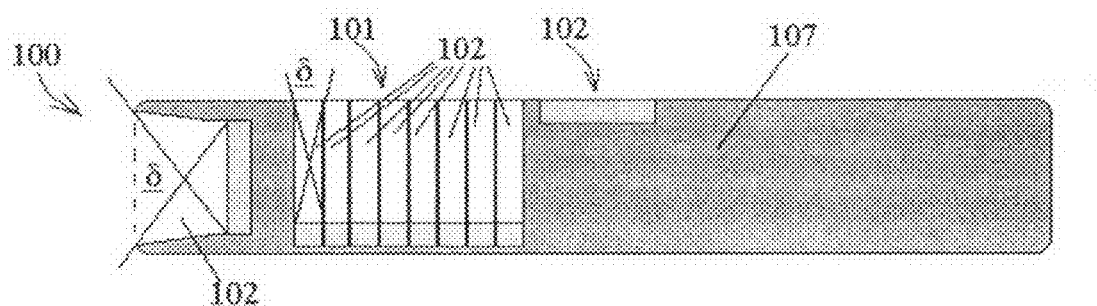
Figure 1I:
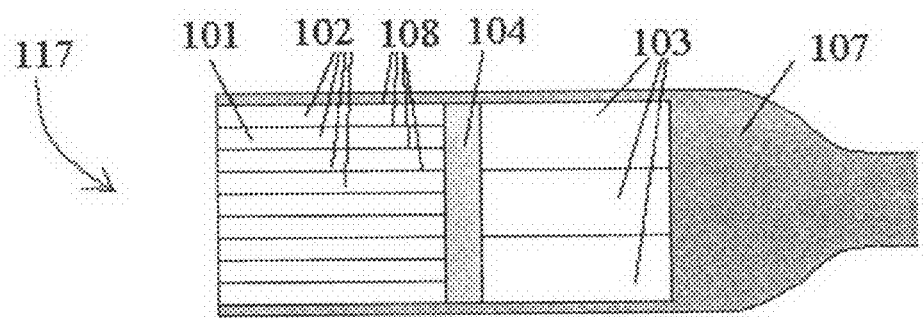

The present embodiments teach providing modifications of the reconstruction and/or imaging processes in order to obtain a reliable reconstruction of the imaged volume. Specifically, the methods teach analyzing the reliability of the reconstruction obtainable from collected emission data over a set of views to determine modifications which are expected to improve reliability. The present embodiments further teach using radioactive-emission measurements to define views for further radioactive-emission measurements of a body structure, to be performed during the current measurement process.

With non-uniform scanning, the amount of information available for different voxels is not uniform, thereby constraining the ability to obtain an accurate reconstruction of the volume. In addition, there may be a need to focus on a region or regions of interest, and to control reconstruction resolution and accuracy where and when necessary. In such cases it is important to provide features and algorithmic components which handle or compensate for the lack of uniformity of information, and are capable of focusing on features or regions of interest, while maintaining short and efficient data acquisition.

In the context of medical imaging the imaged volume corresponds to a body structure, which may include a whole body, portion of a body, target organ and so forth. Those non-limiting embodiments presented below which are directed at imaging a body structure are to be understood as applying to any imaged volume.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1J:
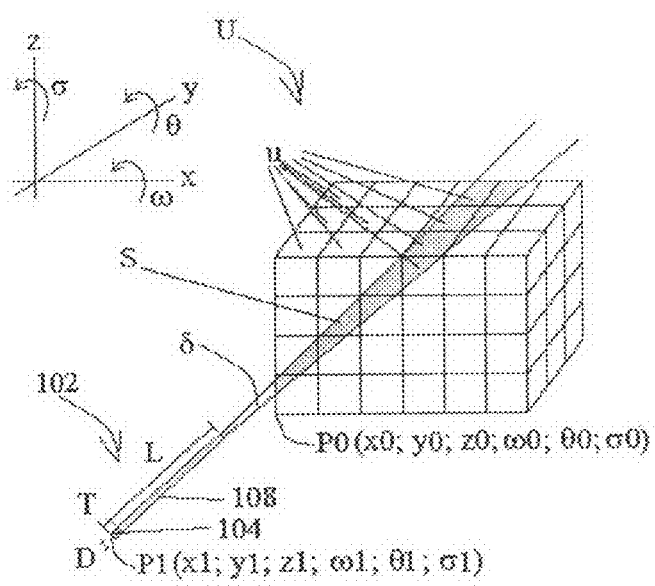
FIGS. 1j and 1k pictorially illustrate a view and viewing parameters associated with it, in accordance with definitions of the present invention.
Figure 1K:
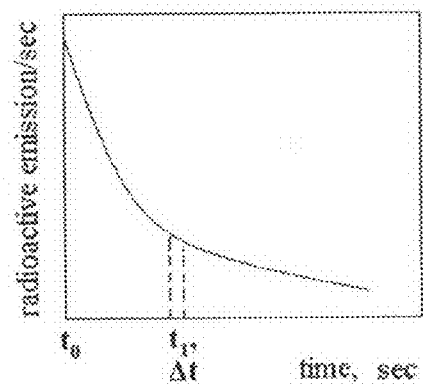

Referring now to the drawings, FIGS. 1j and 1k pictorially illustrate a view and viewing parameters associated with it, in accordance with definitions of the present invention.

Seen in FIG. 1j is a volume U, subdivided into voxels u. The volume U is defined in a six-degree coordinate system $(x;y;z;\omega;\theta;\sigma)$ and has a point of origin $P0(x0; y0; z0; \omega0; \theta0; \sigma0)$. A detecting unit 102 is positioned at a location and orientation $P1(x1; y1; z1; \omega1; \theta1; \sigma1)$. The detecting unit 102 has a detector 104 of a specific detector material of a thickness $\tau_d$, and a collimator 108 of a diameter D and a length L, so as to define a collection angle $\delta$. The location, orientation, and collection angle parameters determine a three-dimensional sector S, which is the portion of the volume U that is within the detector unit's field of view. The probability of detection of a given voxel outside of sector S is negligible, since a photon emitted from the given voxel outside of sector S will have a very low probability of reaching detector 104 through collimator 108.

FIG. 1k schematically illustrates the emission rate of the volume U, as a function of time, given that a radioactive material of a specific half-life has been administered at a time T0.

A view may thus be defined as a group of nonzero probabilities of detecting a radioactive emission associated with all the voxels that form sector S (FIG. 1j).

A view is sometimes referred to as a projection, and the two terms are synonymous. Furthermore, a view defined over the sector S can be naturally extended to be defined over the group of all voxels in the volume U, by simply associating a zero probability with every voxel outside the sector S. This enables applying mathematical operations over the entire volume U.

The viewing parameters, which are the factors affecting the detection of radioactive emissions, are as follows:

i. Location and Orientation Parameters:
   a location and an orientation in a six-dimensional space, $P1(x1; y1; z1; \omega1; \theta1; \sigma1)$, with respect to the origin $P0(x0; y0; z0; \omega0; \theta0; \sigma0)$ of the volume U, in which the detecting unit 102 is positioned;

ii. Detector-Unit Parameters:
   the detector unit geometry (e.g. length L, diameter D, and/or collection angle $\delta$), which together with the location and orientation parameters, P1(x1; y1; z1; ω1; θ1; σ1) with respect to the origin P0(x0; y0; z0; ω0; θ0; σ0) define the sector S;

the septa thickness τ, which affects the probability that a photon that enters the collimator will reach the detector as well as crosstalk effects (which occur when a photon which entered a neighboring cell penetrates the collimator and reaches the detector), hence, the detector efficiency the detector material, which affects the detector efficiency; and the detector thickness $\tau_d$, which affects the detector's stopping power, hence, its efficiency;

iii. Attenuation Parameters:

attenuation properties of all the voxels within the sector S, as they affect the probabilities that radioactive emissions from a specific voxel within the sector S will reach the detector, wherein different voxels within the sector S may have different attenuation properties, since several types of tissue may be involved;

iv. Time Parameters:

since the radiopharmaceutical decays with a specific half-life, the time $t_1$ since administration, and the duration of the measurement $\Delta t_1$, affect the number of emissions that occur during the radioactive-emission measurement.

v. Radiopharmaceutical Parameters:

The half-life $t_{1/2}$, of the radiopharmaceutical, the types of radioactive emission, whether gamma or beta, and the energies of the radioactive emission affect the probability of detection.

Some of these viewing parameters are fixed for a particular situation. Specifically, the tissue attenuation parameters are given. Additionally, the time $t_1$ since administration of the radiopharmaceutical is generally governed by the blood pool radioactivity, since it is generally necessary to wait until the blood pool radioactivity dies out for low-level detection to be possible. For the remaining viewing parameters, optimization may be carried out.

To recapitulate the problem described above, an intensity distribution I, in terms of radioactive emissions per seconds, is defined over the volume U, forming our input space. Volume U comprises a set of basic elements u (e.g., pixels in two dimensional spaces, voxels in three dimensional spaces), and I(u) is the intensity in a given basic element u∈U. A view (also denoted a projection) φ∈Φ is defined by the set of probabilities {φ(u):u∈U}, where φ(u) is the probability of detecting a radioactive emission from a voxel u, as defined by viewing parameters, such as the physical and geometrical properties of the detecting unit, as well as the attenuation parameters of the viewed volume U, and the time parameters. A measurement is obtained by choosing a view φ∈Φ, and then sampling according to the viewing parameters.

As shown in Eqn. 1b, the relationship between the measurements, y, and the emission intensities over the body structure may be represented as y=Poisson(ΦI). The reconstruction problem we are faced with is to calculate the intensity vector I from the measurement vector y, given a known probability matrix Φ.

Applying SVD analysis to the probability matrix Φ, we obtain:

$$\Phi=UDV^t => y=\text{Poisson}(UDV^tI) \qquad (16)$$

where U and $V^t$ are unitary matrices, and D is a diagonal matrix containing the singular values of Φ. Any destabilizing singular values in D are likewise destabilizing to the Poisson process. Specifically, those elements of I (or linear combinations of elements) for which insufficient data is available are equivalent, regardless of whether or not the photon emissions are modeled as Poissonian.

The following description is directed at a non-limiting preferred embodiment wherein the relationship between the measurements y and intensities I are modeled as a set of linear equations, y=ΦI, for the purposes of reconstruction. This model is suitable for least squares optimization when photon emissions have a Gaussian distribution, and thus may be reasonably applied when the measured counts (i.e. y) are relatively high. However the embodiments are extendable to modeling the emissions as Poissonian. In a preferred embodiment, when a given voxel or voxels are not within Gaussian range, the y values of several low-intensity views are combined and set equal to the sum of all the related linear equations, in order to bring the total count into Gaussian range.

Assuming intensities with a Gaussian distribution, then by applying SVD to the present inverse problem, I is obtained as:

$$I=VD^{-1}U^t y \qquad (17)$$

As discussed above, the condition number of D may serve as an indicator of the stability of the reconstruction, particularly during an iterative reconstruction process. Furthermore, known techniques such truncated SVD may be used for optimization and reconstruction purposes.

The present embodiments are of a method, apparatus, and system which analyze the reliability of the reconstruction possible by a given imaging constellation, and define modifications in order to improve the quality of reconstruction. The modifications may be to the reconstruction and/or data collection aspects of the imaging process. As described below, the modifications may use active view selection during imaging and/or to guide non-uniform scanning of the imaged volume.

Figure 2A:
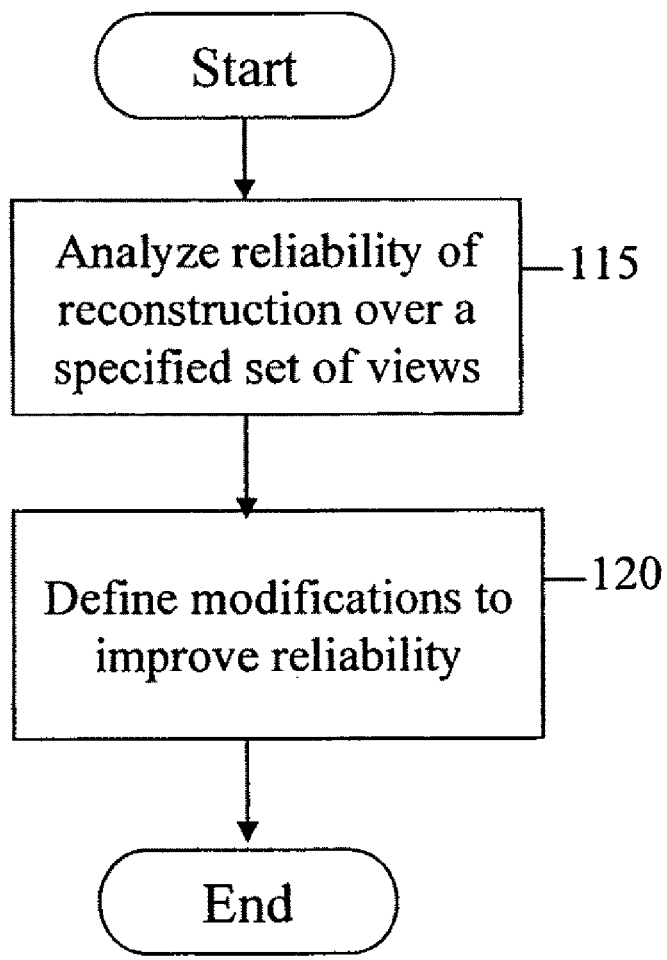
FIG. 2a is a simplified flowchart of a method for stabilizing the reconstruction of an imaged volume, according to a preferred embodiment of the present invention.

Reference is now made to FIG. 2a, which is a simplified flowchart of a method for stabilizing the reconstruction of an imaged volume, according to a preferred embodiment of the present invention. In step 115, an analysis of the reliability of reconstruction of a radioactive-emission density distribution of the volume is performed. The analysis is made to determine the reliability of the data which may be collected by radioactive-emission measurements taken over a specified set of views. In step 120, modifications to improve reliability of reconstruction are defined in accordance with the analysis. The modifications may involve a change or adaptation of the reconstruction process and/or a change or adaptation of the data collection process. Both the analysis and modification aspects of the present embodiment are described in detail below.

The present embodiment tailors the reconstruction and/or data collections processes in order to obtain a more accurate reconstruction of the imaged volume. Low reliability data may cause large errors in the reconstruction process. As a result the reconstruction process may be noisy and unstable, and fail to converge properly. The reconstructed image may contain artifacts, unsupported frequencies and other errors.

The present embodiments are applicable to all stages of the imaging and/or reconstruction processes. The analysis may be performed prior to data collection, in order to define a scanning procedure which provides high-reliability data. During data collection, the scan pattern may be adapted or views may be added (e.g. active vision/adaptive scanning), utilizing the new information provided by the collected data. After data collection, modifications may be made to the reconstruction process in order to counteract the effects of unreliable data and non-uniformities, and to improve reconstruction accuracy and stability.

In a first preferred embodiment, the analysis of the reliability of reconstruction is based upon on analysis of the singular values of the probability matrix Φ. A non-limiting preferred embodiment of such an analysis is presented below.

Figure 2B:
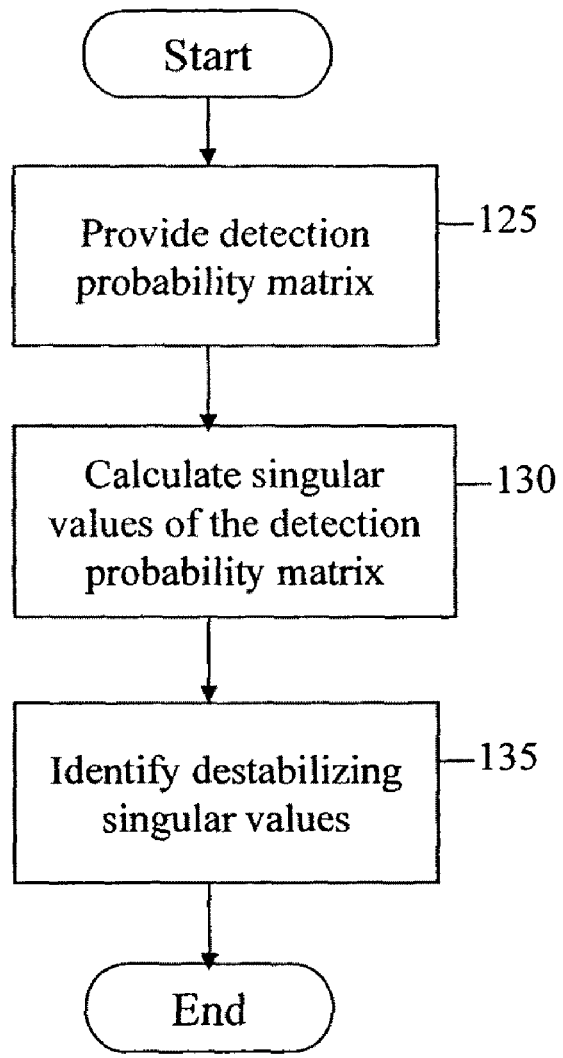
FIG. 2b is a simplified flowchart of a method for analyzing a detection probability matrix, according to a preferred embodiment of the present invention.

Reference is now made to FIG. 2b, which is a simplified flowchart of a method for analyzing a detection probability matrix, according to a preferred embodiment of the present invention. In step 125, a detection probability matrix is provided. As described above, the detection probability matrix gives the detection probability for each of the views over the voxels of the volume. More explicitly, in the preferred embodiment each view has an associated row in the detection probability matrix. The values in a given row are derived from the probability of detection of a photon emerging from each of the voxels of the volume, by a detector at the associated view. In step 130, the singular values of the detection probability matrix are calculated. In the preferred embodiment, the singular values are calculated by employing SVD on the detection probability matrix. Performing SVD on the detection probability matrix enables easy implementation of stabilization methods such as truncated SVD for stabilizing the reconstruction process. In step 135, those singular values which may have a destabilizing effect on the reconstruction process are identified as destabilizing singular values.

In the preferred embodiment, a measure of the reconstruction reliability (denoted herein the reliability measure) is determined. The reliability measure is used for determining if any modification of the imaging and/or reconstruction processes is required, or if a stable reconstruction is possible without such modification.

Preferably, the condition number of the probability matrix is utilized as a reliability measure. If the condition number is satisfactory the reconstruction may be considered stable, with no need for modification. Preferably, the identifying of destabilizing singular values is performed only if the condition number is below a specified magnitude.

In an alternate preferred embodiment, the information-theoretic Fisher information is calculated as a reliability measure from intensity distributions provided of the imaged volume. An intensity distribution may be obtained either as an emittance model created prior to the data measurement process, or as an intermediate result of the reconstruction process. The Fisher information is described in detail below, in the context of the reliability criterion for active vision.

In the preferred embodiment, the identification of destabilizing singular values is performed as follows. The ratio of the largest singular value to each of the remaining singular values is calculated. A singular value for which the ratio is above a specified threshold is considered destabilizing. One may consider that if the effects of the destabilizing singular values upon the reconstruction are eliminated, the condition number of the detection probability matrix is effectively below the threshold.

Preferably, unreliable voxels or combinations of voxels associated with a given destabilizing singular value are identified. The intensity levels of such unreliable voxels or combination of voxels are unsupported in the collected emission data, due to the destabilizing effects of the associated singular value. Therefore the accurate reconstruction of such voxels and/or combinations is unlikely, and may destabilize the reconstruction process. The destabilization of the reconstruction by unsupported voxels may lead to artifacts and unsupported frequencies in the reconstructed intensities. These effects are not necessarily limited to the unsupported regions, but may extend into other portions of the volume and create artifacts there as well.

The voxels and linear combinations of voxels associated with a singular may be determined via SVD decomposition of the intensity distribution matrix Φ. The matrix V obtained by SVD decomposition of Φ indicates voxels or linear combinations of voxels whose intensity after reconstruction is most highly affected by each of the singular values in D. Each row of V indicates a weighting associated with a given singular value for each voxel in I. Consider the following example of a volume with four voxels i1-i4:

$$y = UDV^T I \qquad (18)$$

$$= U \begin{bmatrix} e_1 & & & \\ & e_2 & & \\ & & e_3 & \\ & & & e_4 \end{bmatrix} \begin{bmatrix} v_{11} & v_{12} & v_{13} & v_{14} \\ \dots & & & \dots \\ \dots & & & \dots \\ v_{41} & v_{42} & v_{43} & v_{44} \end{bmatrix} \begin{bmatrix} i1 \\ i2 \\ i3 \\ i4 \end{bmatrix}$$

$$= U \begin{bmatrix} \dots \\ \dots \\ \dots \\ e_4(v_{41}i1 + v_{42}i4 + v_{43}i3 + v_{44}i4) \end{bmatrix}$$

In a first example, assume that e4 is a destabilizing singular value, and that the fourth row of V, $v_4$, equals [0.001 0.01 0.97 0.015]. Examining $v_4$ it is seen that the coefficient for the single voxel i3 is significantly larger the coefficients of the other voxels. It is therefore quite apparent that the reliability of data regarding voxel i3 is particularly low, and it is unlikely that i3 can be accurately reconstructed. In this example, the preferred embodiment is to perform smoothing of i3 relative to the neighboring voxels. Smoothing may be a practical approach where an inaccuracy occurs in spatially localized regions of the volume. An exemplary criterion to determine which voxels should be smoothed, is to select voxels whose corresponding coefficient of $v_i$ is above a certain threshold.

In a second example, assume that e3 is a destabilizing singular value, and that the third row of V, $v_3$, equals [0.5 −0.5 0.5 −0.5]. In the present example, the unreliability of the data relates to a combination of voxels which may be distributed over the volume, rather than to an independent, spatially located voxel or group of voxels. In the present example, the reliability of data regarding the linear combination 0.5i1−0.5i2+0.5i3−0.5i4, as reflected by measurements y, is low, which may lead to instability and inaccuracies during reconstruction. Since there are no dominant voxels it may be less effective to perform smoothing. Instead, the preferred embodiment is to constrain intensities of the combination of voxel intensities between iterations.

A proposed approach for applying such a consrtaint is as follows. Given a reconstructed intensity vector I', modify the intensities prior to performing the next iteration as follows:

$$I' => I' - v_k \alpha (v_k^T I) \qquad (18)$$

where $v_k$ is the row of V associated with a destabilizing singular number, $e_k$, and α is a proportionality factor which may be related to the magnitude of $e_k$. The effect of the voxel combination on the following iteration is therefore reduced as desired, where the reduction may be correlated with the dominance of the associated singular value.

Preferably, constraints are added during the reconstruction process to reduce or eliminate the effects of the unreliable data associated with destabilizing singular values.

In the preferred embodiment, the modifications include defining constraints on the reconstruction process. The reconstruction may be considered unreliable if one or more destabilizing singular values have been found, and the modifications may be made in order to reduce the effect of the destabilizing singular values upon the reconstruction. Examples of such constraints may include:
1) Smoothing or piecewise smoothing for all or portions of the volume
2) Uniting voxels
3) Subdividing voxels
4) Adjusting the levels of one or more voxels after a reconstruction iteration
5) Constraining the input data
6) Performing reconstruction with differing resolutions for different portions of the volume The above exemplary constraints are now discussed in turn.

Smoothing a reconstructed image is performed by calculating the intensity level of a voxel based on the intensities of surrounding voxels, in order to control the magnitude and rate of the fluctuations in intensities between voxels. For example, the intensity of a given voxel may be corrected to better reflect its value as an average of the surrounding voxels. Smoothing may be performed over the entire volume, or only on portions of the volume deemed unreliable.

When a non-uniform scan is performed, it is possible that not all directions surrounding a voxel will have equal support. It may therefore be easier to distinguish voxel from some neighbors than from others. In the preferred embodiment, smoothing is performed directionally. In directional smoothing, the smoothing is weighted more strongly in certain directions than in others.

In a first example, directional smoothing is used to overcome the limitations of unreliable data by smoothing the voxel in the weaker directions. In a second example, a higher resolution is available for some portions of the volume than is available in other portions. If it is important to obtain a reconstruction having a uniform resolution, directional smoothing may be applied reduce the resolution in highly reliable portions of the volume to the resolution obtainable elsewhere.

A directional smoothing policy may be based on the Fisher information measure, which provides directionality information. The Fisher information matrix indicates directionality and cross-relationships between voxels, but may be difficult to calculate. In the preferred embodiment, a scalar Fisher information is calculated for groups of views, where each group is localized in a given direction. The scalar Fisher information measures may then be analyzed together, in order to determine the relationships between the different directions.

Low reliability voxels may be united or combined with surrounding voxels in order to increase their reliability. Voxels may combined by assigning the intensity level of a neighboring high-reliability voxel to the low-reliability voxel. Voxel merging may be carried out more extensively, by repeatedly merging the lowest reliability voxel with one of the neighboring voxels to form an aggregate of voxels, until no voxel is left with a reliability below a threshold. It will be appreciated that the aggregate voxels have a lower resolution locally, but all other regions with good coverage remain of high resolution, according to their coverage.

An opposite approach for high-reliability portions of the volume is to subdivide high-reliability voxels into smaller voxels in order to improve resolution while still achieving a required reliability. For example, if there are 1000 different views independently covering 1 cubic cm and almost not affected by the surrounding voxels, then theoretically that volume can be divided up to about 1000 voxels, if the views create a linearly independent set of equations with a good condition number.

A further possible modification of the reconstruction process may be to adjust the effect of certain unreliable voxels or linear combinations of voxels after each of one or more iterations of the reconstruction process. For example, the magnitude of unreliable voxels or combinations of voxels associated with a destabilizing singular value may be reduced towards zero or towards the value of neighboring voxels by a specified factor, possibly in proportion to their respective weightings in the associated row of matrix V and/or to the associated singular value.

An additional possible modification is to constrain the value of the input. For example, a realistic range of counts may be defined overall or per view based on view parameters, typical spatial structures and the like. Examples include adding a prior constraint such as a gamma distribution of intensities, a constant or piecewise-constant progression of intensities, a linear or piecewise-linear progression of intensities, smoothing or piecewise smoothing constraints, an intensity distribution based on the shape of or magnitude of the object being scanned (possibly determined during a pre-scan), or a maximal or known range of expected intensities, The reconstruction process may be performed in a manner that obtains varying resolutions over the volume. In one approach, the entire volume is defined as a single huge voxel, and split over the reconstruction iterations to form smaller voxels. The process is performed repeatedly over all or some of the voxels of the volume, as long as the result of the split maintains a reconstruction reliability high enough for stable results.

In a further preferred embodiment, the information-theoretic Fisher information is used as a reliability measure. Modifications to the reconstruction and/or data collection processes may be performed when the Fisher information is deemed to be outside a specified range. The calculation of the Fisher information is described in detail below, in the context of the reliability criterion for active vision. The Fisher information may be calculated from the results of a previous reconstruction iteration, or, initially, from an emittance model provided of the imaged volume.

The following addresses a preferred embodiment in which the modification is implemented by defining views for imaging the volume. The defined views serve to guide the data collection process in order to obtain measurements which enable performing a stable and accurate reconstruction of the intensity distribution of the volume. In this manner, detecting resources may be invested effectively in order to improve reconstruction reliability. Scanning resources include, for example, detector dwell time, number of detectors, angular and translational increments, and the like—features that increase the amount of data collection.

Such modification may be performed when a region is interesting but is still left with coarse resolution, so as to allocate more scanning resources, such as dwell time, number of detectors, angular and translational increments, to cover that region and to form more independent views such as to increase the reliability of the reconstruction of that area. Preferably, the views are defined so as to obtained a desired resolution over the region of interest.

The defined views may yield a non-uniform scanning procedure. A scanning density may be specified by the angular and translational increment size, or steps, the smaller the increment, the higher the density. Additionally, the scanning density may be defined by the acquisition time at each position—the longer the time, the higher the density.

Non-uniform scanning may be defined by specifying varying scan densities for imaging the volume. For example, the modification may entail adjusting a local scanning density to scan a region of interest with high density, and to scan other regions with low density.

The non-uniform scans may relate to non-uniform angular steps of the detector along a sweep, non-uniform detector translational steps, or different steps by different detectors. Some detectors may employ dense steps and others may employ sparse steps, for example, based on active vision as taught hereinbelow.

The scan density may be adapted to the distance to the object of interest. Since resolution decreases with distance, the higher density may compensate for increased distance.

Additionally or alternatively, the angular steps may increase in density when scanning a region of interest, and decrease in density, when scanning other portions of the volume.

Furthermore, more than one region of interest may be scanned with dense steps, simultaneously. The two regions of interest may be, for example, a tissue region and a blood pool region. This has applicability, for example, to dynamic studies of blood perfusion, by providing even scanning resources both to the blood and to the tissue.

Additionally, convex scans may be employed.

Variable scans, where a same region is scanned first with a first density and then with another density, may be employed. Alternatively, a same region may be scanned by a first group of detectors with a first density and then by a second group of detectors with another density, concurrently, or at different times. Thus the same region is scanned with at some density by a given detector and at a different density by another detector.

In a further preferred embodiment, view definition is performed dynamically during radioactive-emission measurements of the volume. The definition of further views for measurement during the data collection process is denoted active vision herein and is described in detail below. Active vision may be performed independently or in conjunction with the present preferred embodiment of stabilizing the reconstruction of an imaged volume.

In the preferred embodiment, the method includes the further step of iteratively reconstructing the radioactive-emission density distribution of the volume, preferably by EM estimation. Reconstruction reliability is preferably evaluated after every iteration.

Figure 2C:
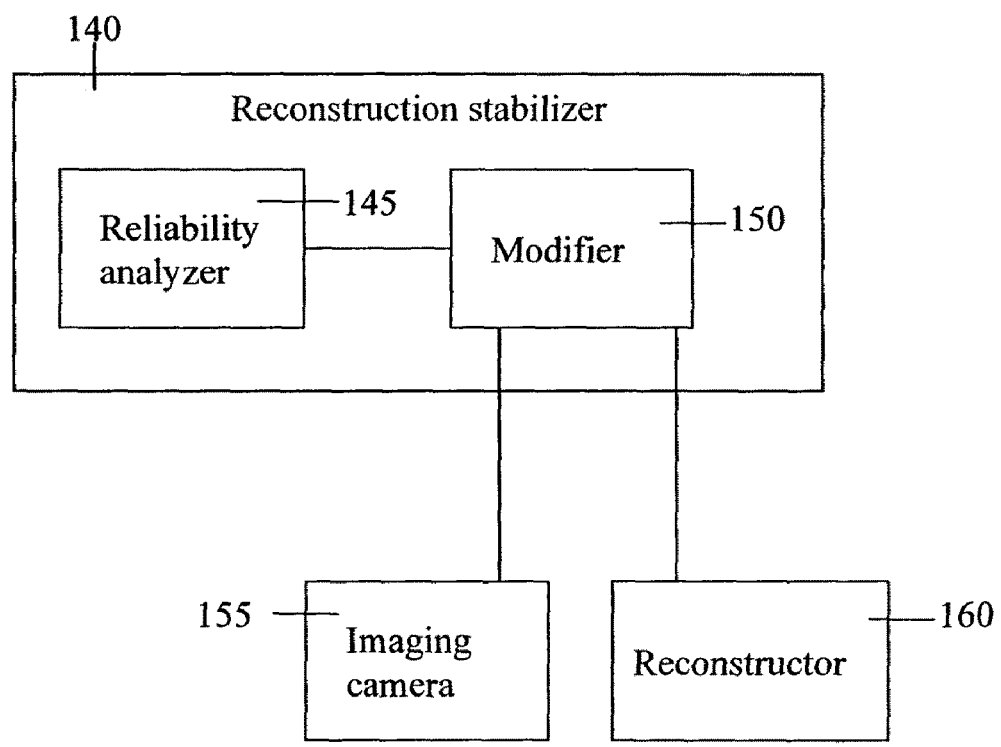
FIG. 2c is a simplified block diagram of a reconstruction stabilizer, according to a preferred embodiment of the present invention.

Reference is now made to FIG. 2c, which is a simplified block diagram of a reconstruction stabilizer, according to a preferred embodiment of the present invention. Reconstruction stabilizer 140 includes reliability analyzer 145 which analyses the reconstruction reliability of a radioactive-emission density distribution of a volume. The reconstruction reliability may be determined from measures such as the condition number of the probability density matrix or the Fisher information, as described above. Modifier 150 defines modifications to improve the reliability of the reconstruction, based on the analysis performed by reliability analyzer 145. Modifier 150 preferably applies at least one constraint to the reconstruction process and/or data collection. The constraints may include applying smoothing, uniting voxels, adjusting the levels of voxels, defining new views or non-uniform scanning, and other constraints described above. The views may be defined before or during emission data collection.

In the preferred embodiment, reconstruction stabilizer 140 is included in a system for generating a three-dimensional image of volume. In the preferred embodiment, the system further includes radiological imaging camera 155 and reconstructor 160. Camera 155 includes detectors capable of independent movement during data acquisition, and which are capable of detecting radiation emitted from the volume thereby to provide radiation data. In accordance with embodiments of the present invention, each block of the imaging camera construction or each detecting unit, where single-pixel detecting units are used, may be provided with at least one, and preferably, two, three, or as many as six degrees of motion such as, for example, rotational motion around the x, y, and z, axis, oscillatory motion about these axes, or translational motion along these axes. Camera 155 thus enables flexible view definition by modifier 150, increasing the likelihood that a reliable reconstruction will be achieved. Reconstructor 160 analyzes the radiation data provided by camera 155 so as to reconstruct a three-dimensional image of the volume.

Reconstructor stabilizer 140 guides camera 155 and reconstructor 160, by providing one or both with the modifications determined to improve reconstruction reliability.

In practice, it is generally necessary to reconstruct volumes at a high resolution (i.e. a large number of voxels) from many measurements. Implementing the techniques described above then requires the manipulation of extremely large matrices. The large size of these matrices poses difficulties both for performing the calculations and for memory management. These difficulties are particularly problematic when active view selection is performed.

In the preferred embodiment, calculations are performed in a localized manner. That is, calculations are performed for different sections of the volume in turn, progressing through the volume until it is covered in its entirety. When calculations are being made of a particular section of the volume, the variables relating to the other sections are "frozen". Thus first a selected section of the volume may be stabilized, so that the reconstruction of following sections is based on data with improved reliability. Localized calculations, such as SVD decomposition, are performed on smaller sub-matrices rather than on a single large matrix, alleviating the difficulties of manipulating very large matrices.

The division of the volume into sections may be devised in any practical way, for example as sequential slices or by another spatial connection. The division may be based on the scan pattern, so that well-supported sections may be stabilized first, followed by less supported section. The division may also or alternately be based on knowledge of the body being imaged, such as its shape or composition. When imaging a body structure, the sections may be based on the known axes or structures of the organ The following embodiments are of a method for determining further views for the imaging of a body structure, denoted active vision herein. Active vision addresses the problem of ensuring that the quality of data gathered during the measurement process is adequate to provide a high quality image. The collected data and/or the image reconstructed from the collected data is analyzed the while the measurement process is taking place. Based on the analysis, further views are defined. Since each view is associated with known values of the viewing parameter(s), selecting a view effectively specifies known viewing parameter values. The defined further views thus define a set of viewing parameter values, which are used during the current measurement process in order to collect data which yields a high-quality reconstruction of the body structure.

Active vision may be performed independently, as described in the embodiments presented below. Additionally or alternatively, active vision may be performed in conjunction with the above-described method for stabilizing reconstruction, by modifying data collection by dynamically providing additional views to improve reconstruction reliability (see FIG. 17).

The following embodiments are not confined to a specific reconstruction algorithm. Further views are preferably defined based on one or more of the following:
1) Detector photon count
2) Geometric properties of the reconstructed body structure
3) Information theoretic measures that quantify the quality of the data fed to the reconstruction algorithm Each of these criteria is discussed in detail below.

Figure 2D:
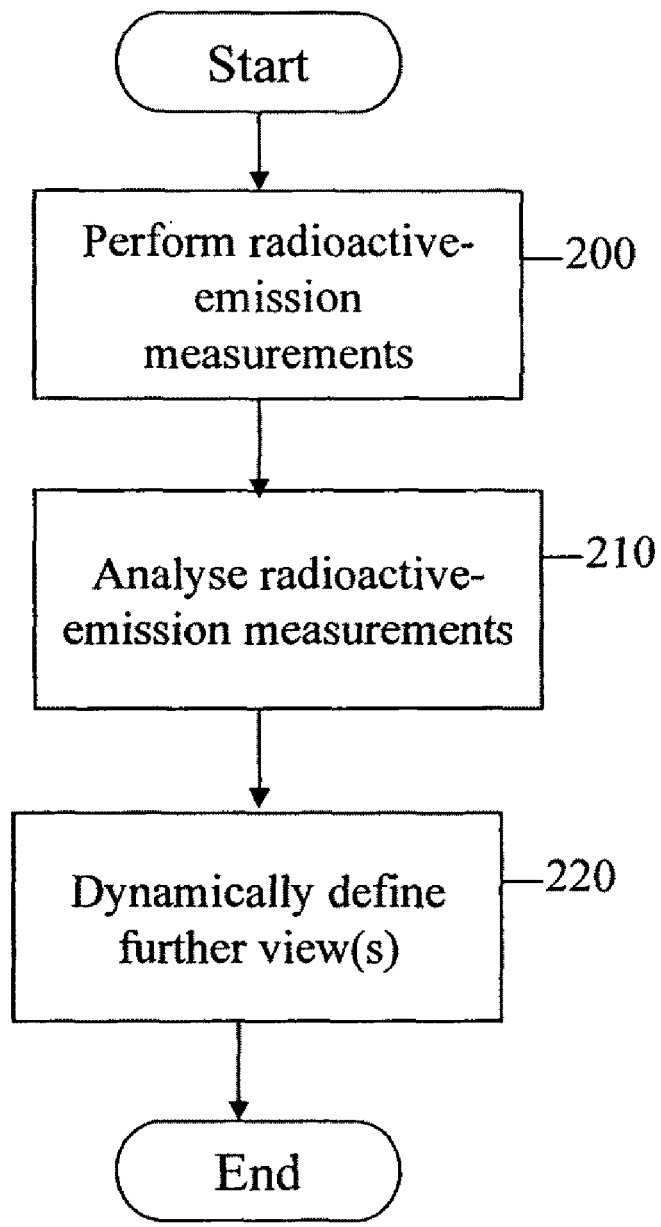
FIG. 2d is a simplified flowchart of a method of performing radioactive-emission measurements of a body structure, according to a preferred embodiment of the present invention.

Reference is now made to FIG. 2d, which is a simplified flowchart of a method of performing radioactive-emission measurements of a body structure, according to a preferred embodiment of the present invention. In step 200, radioactive-emission measurements of the body structure are performed at predetermined views, preferably in vivo. Preferably the measurements are performed for diagnostic purposes. These predetermined views are selected prior to the measurement process, based on a model of the body structure being imaged. In the model more and less informative viewing directions have been identified. The predetermined views of step 200 preferably include those views expected to be informative, based on an analysis of the model.

Preferably the body structure is all or a portion of: a prostate, a heart, a brain, a breast, a uterus, an ovary, a liver, a kidney, a stomach, a colon, a small intestine, an oral cavity, a throat, a gland, a lymph node, the skin, another body organ, a limb, a bone, another part of the body, and a whole body.

In step 210 the radioactive-emission measurements are analyzed. Preferably the analysis includes one or more of:
1) Analyzing detector photon count(s)
2) Analyzing detector photon count rate(s)
3) Identifying detector saturation
4) Reconstructing a body structure image from emission measurements
5) Identifying geometric properties of the reconstructed image
6) Applying information-theoretic measures to the reconstructed image In step 220, further views for measurements are dynamically defined, based on the analysis performed in step 210. Preferably, each of the views is associated with viewing parameters selected from the group consisting of: detector unit location, detector unit orientation, collection angle, and measurement duration. Defining a view consists of providing a value for each of the parameters associated with the given view. The analysis (step 210) and/or dynamic view definition (step 220) may take into account external parameters including: measurement duration, time elapsed from the administration of the pharmaceutical to the measurement, radiopharmaceutical half life, radioactive emission type, and radioactive emission energy.

Each of these analysis techniques, and their application to view definition, is now discussed in turn. While each of the analysis/view determination techniques is discussed as a separate embodiment, multiple techniques may be used together to obtain the desired image quality.

In a first preferred embodiment, a photon count analysis ensures that the photon count at a given view yields an acceptable measurement error. As discussed above, the radiative emissions of the body structure being imaged is a Poisson process. In a Poisson process the Poisson noise grows inversely to the square root of the number of photons detected. In other words, if N photons are collected from a given view, the resulting signal to noise ratio (SNR) equals:

$$SNR = N/\sqrt{N} = \sqrt{N} \qquad (19)$$

The unprocessed detector photon count at a given view thus provides significant information regarding the quality of the information obtained at a given view. If the photon count is too low, it may be desired to continue to collect photons at the current location/orientation in order to obtain a satisfactory SNR. Alternatively, it may be determined that enough photons have already been collected, and to terminate the current view and move on to the next view.

The analysis is preferably performed by defining a global or local required measurement error, and comparing the square root of the obtained photon count to the required measurement error. Photon count analysis can be applied to the current and/or previous views. When a photon count of a current view is found to be too low, the duration of the current view is preferably extended in order to obtain the required error value. When a photon count of a past view is found to be too low, an emission measurement at substantially the same location and orientation but having a longer duration than previously is preferably performed. Alternately or additionally, the collection angle at the given location/orientation is preferably increased.

In an additional preferred embodiment, a detector photon count is analyzed to identify detector saturation at a given view. Preferably, when a detector is determined to have saturated, a new view or views are selected to reinforce those views that have saturated. In an alternate preferred embodiment, further views are defined to avoid highly-radiating portions of the body structure.

In a second preferred embodiment, a photon collection rate at a given view is analyzed to determine if it is within a specified range. In the preferred embodiment, the photon count rate is used to identify regions of high or low interest. In prostate imaging, for example, a region of high interest may be identified by a high photon rate, indicative of a tumor. In a second example, a region of high interest may be identified in heart imaging by a low photon rate, indicative of non-functional tissues. After one or more areas of high and/or low interest are found, further views are preferably defined by selecting views to concentrate on regions of high interest and/or to avoid regions of low interest. It is thus possible to zoom in on a suspected pathology without repeating the emission measurement process.

In a further preferred embodiment, the analyzing of step 210 includes reconstructing a radioactive-emission density distribution of the body structure. Reconstruction may be performed according to any applicable technique known in the art. The reconstruction is then used as the basis for further analysis.

Reconstruction based on the data collected from the predetermined views provides information regarding the quality of information obtained from the preceding measurements, and which further views are likely to be most informative. Selecting new views based on reconstruction is intended to bring us into viewing from the more informative views or combinations of views.

Figure 3:
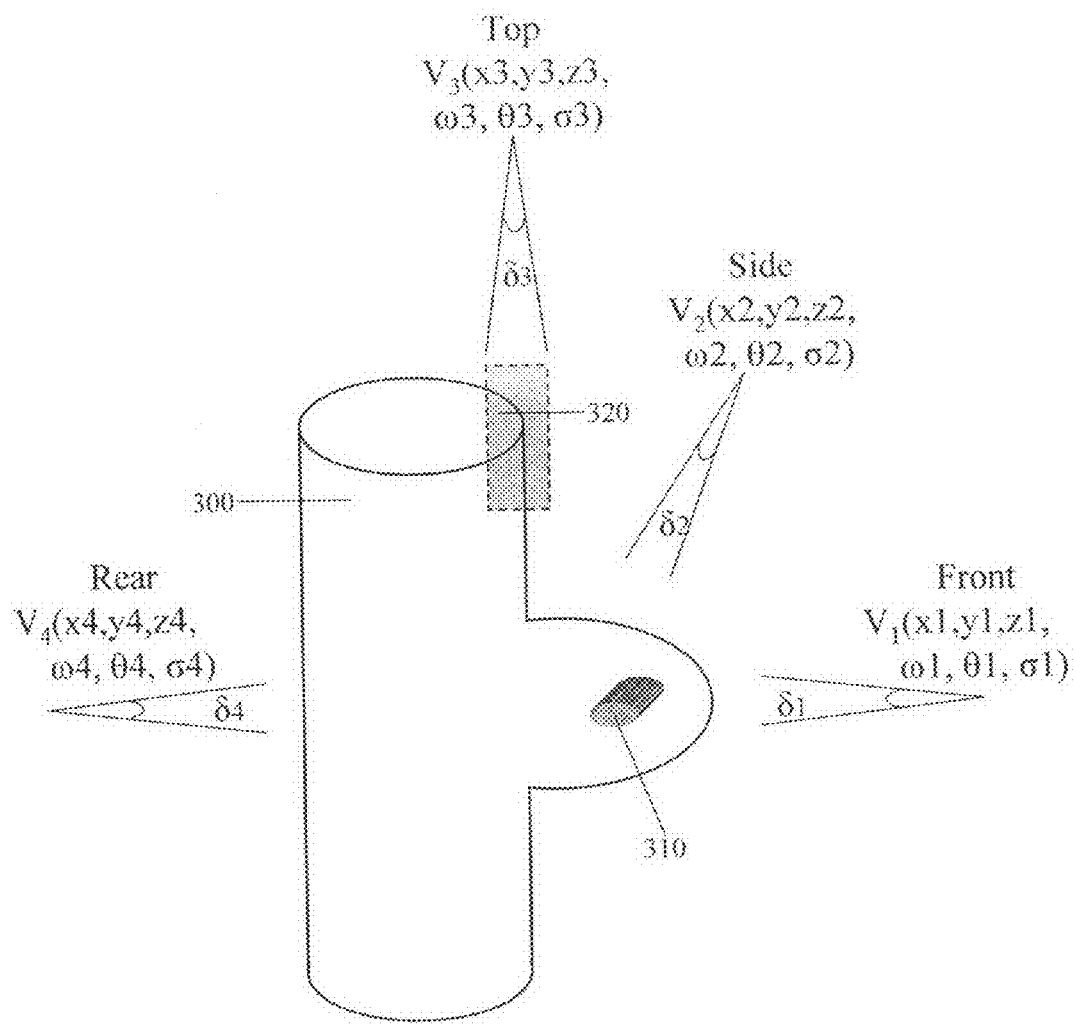
FIG. 3 shows an object shaped as a cylinder with a front protrusion, and having a high-emittance portion (hotspot).
Figure 4A:
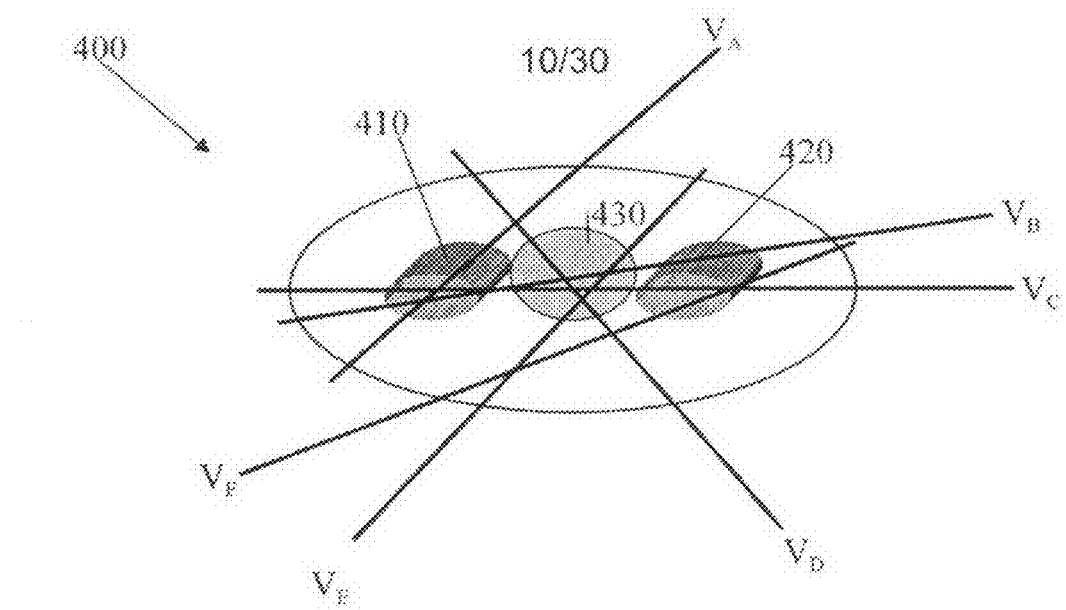
FIG. 4a illustrates an object having two high-emission regions of interest.
Figure 4B:
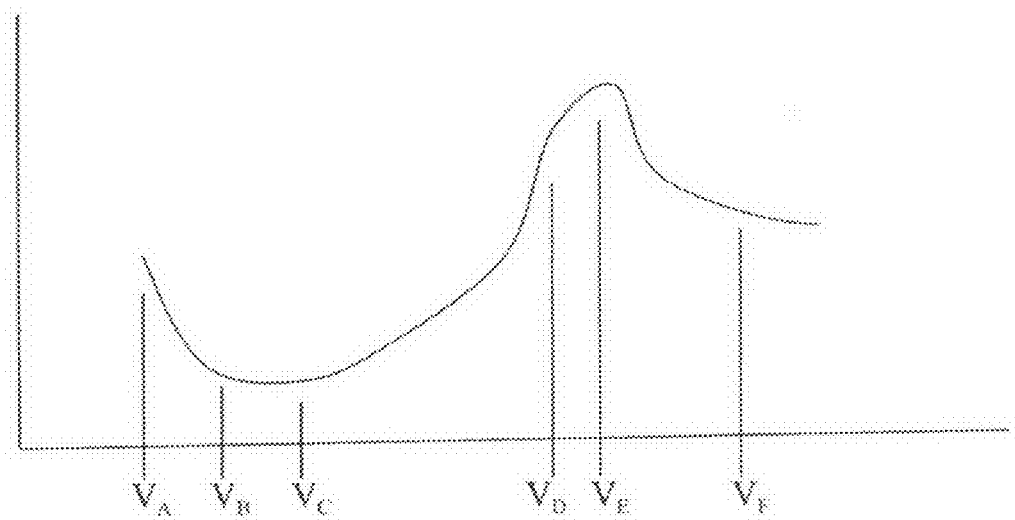
FIG. 4b illustrates the added information provided by each of views $V_A$ to $V_F$.

Reference is now made to FIGS. 3 and 4a-4b, which pictorially illustrate how different views provide differing types and quality of information. FIG. 3 shows an object 300 shaped as a cylinder with a front protrusion, and having a high-emittance portion (hotspot) 310. Four views of object 300 are shown, which can be seen to provide different levels of information. Front views, such as $V_1$, provide little information regarding the shape of object 300 and have relatively little attenuation between the detector and hotspot 310. Side views, such as $V_2$, provide edge information regarding the object shape or profile, and when correlated with front views help locate hotspot 310 spatially within object 300. Top views, such as $V_3$, provide information regarding the cylinder edge region 320. Finally, rear views, such as $V_4$, are uninformative about the shape of object 300 and have high attenuation relative to hot region 310.

FIGS. 4a and 4b demonstrate how the proper selection of views may improve the quality of information obtained for the body structure, for example in distinguishing between two regions of interest within a given volume.

FIG. 4a illustrates an object 400 having two high-emission regions of interest (ROI), 410 and 420. For clarity the views $V_A$ to $V_F$ are shown as lines in FIG. 4a, however in practice they will each have a finite collection angle δ. The position of ROIs 410 and 420 are assumed to have been estimated based on a model of object 400 and/or a previously performed prescan. The goal of the present invention is to select an additional new view or views which increase the information we have regarding the separation of ROIs 410 and 420 within object 400.

In simple terms, consider the object as having three regions: ROI 410 with intensity $I_1$, ROI 420 with intensity $I_2$, and a low-emission region 430 between the two ROIs with intensity $I_3$. The detected intensity at a given detector is proportional to $I_n/r_{ni}^2$, where $I_n$ is the emission intensity of region n and $r_i$ is the distance of region n from detector $V_i$.

FIG. 4b illustrates the added information provided by each of the shown views, $V_A$ to $V_F$. Views $V_B$ and $V_C$ collect emissions from all three regions, and are background intensity by a factor of at least (1+α), where α is a parameter specified by the user. In practice, a hotspot is usually detectable only if the radiation levels within the hotspot are higher than the background level by a factor of 1.5-2. α is therefore typically defined between 0.5-1. However, the detectability of a hotspot rises as the radioactive intensity of the body rises, raising the photon count. Thus, a lower value of α may be used when the measured body structure is in a state of high-intensity emittance. For example, a body structure may be characterized by relatively high emittance immediately following the administration of the radiopharmaceutical, and be characterized by lower emittance at a later time.

In a second preferred embodiment, a suspected organ target is defined as a low-emittance portion of the reconstruction. In heart imaging, for example, a suspected organ target is defined as a low-emittance portion of the reconstruction, indicating non-functional tissues. A low-emittance portion is characterized by an intensity that is lower than the background intensity by a factor of at least (1+β), where β is a parameter specified by the user.

In the preferred embodiment the further views are used immediately for radioactive-emission measurements. The results of the new measurements are then used in another analysis to define new further views for additional measurements. The radioactive-emission measurements may then be said to be performed iteratively.

Figure 5A:
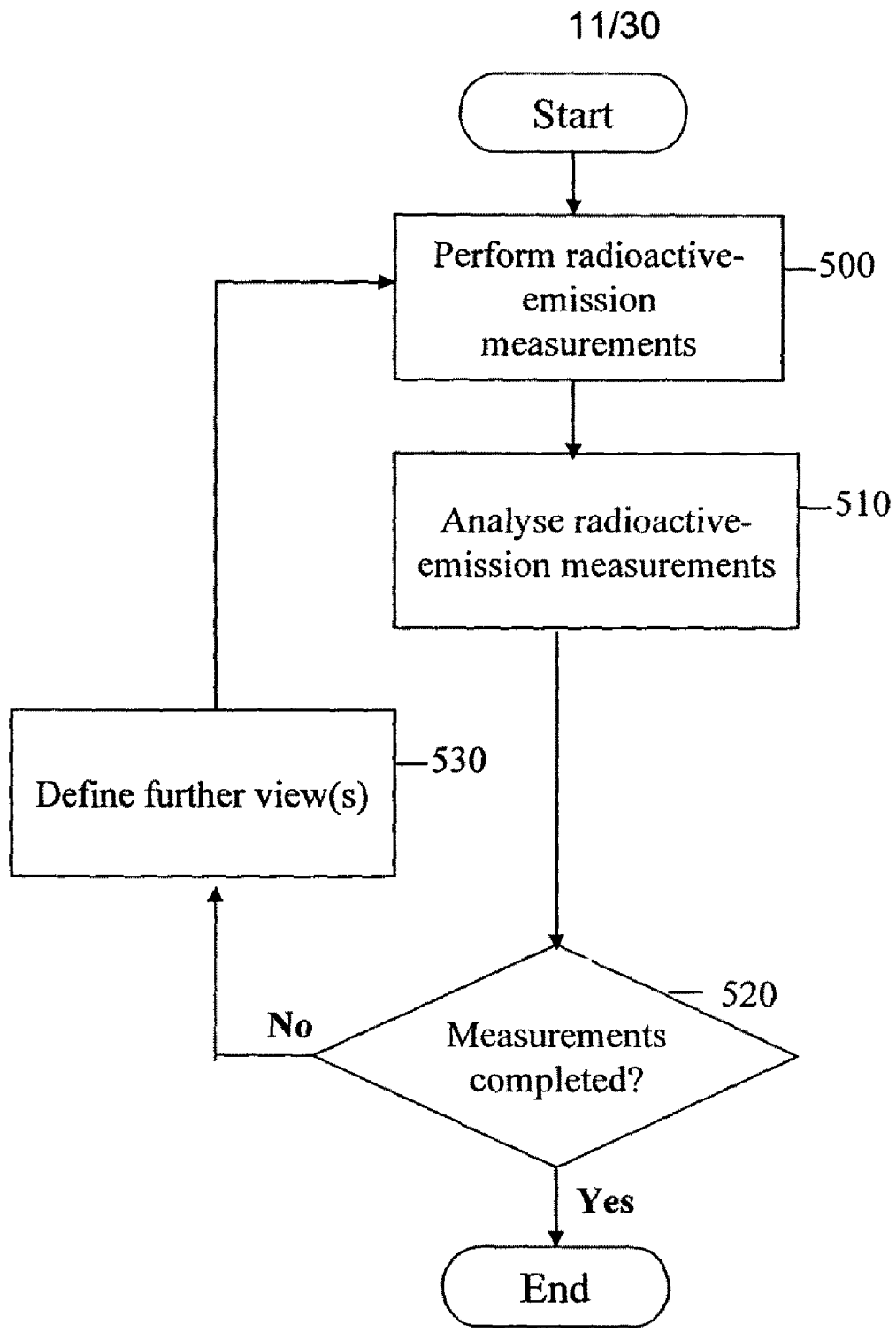
FIGS. 5a and 5b are simplified flowcharts of iterative methods of performing radioactive-emission measurements of a body structure, according to a first and a second preferred embodiment of the present invention.

Reference is now made to FIG. 5a, which is a simplified flowchart of a iterative method of performing radioactive-emission measurements of a body structure, according to a first preferred embodiment of the present invention. In step 500, radioactive-emission measurements of the body structure are performed at predetermined views. In step 510, an analysis is performed of the previously performed emission measurements. In step 520 a decision is made whether to continue with further measurements. If yes, in step 530 further views are defined based on the analysis. Subsequent iterations continue until the decision to end the emission measurement process. After the first iteration, the analysis performed at a given stage may include consideration of all or on part of the measurements performed during one or more previous iterations, in addition to the new measurements.

Figure 5B:
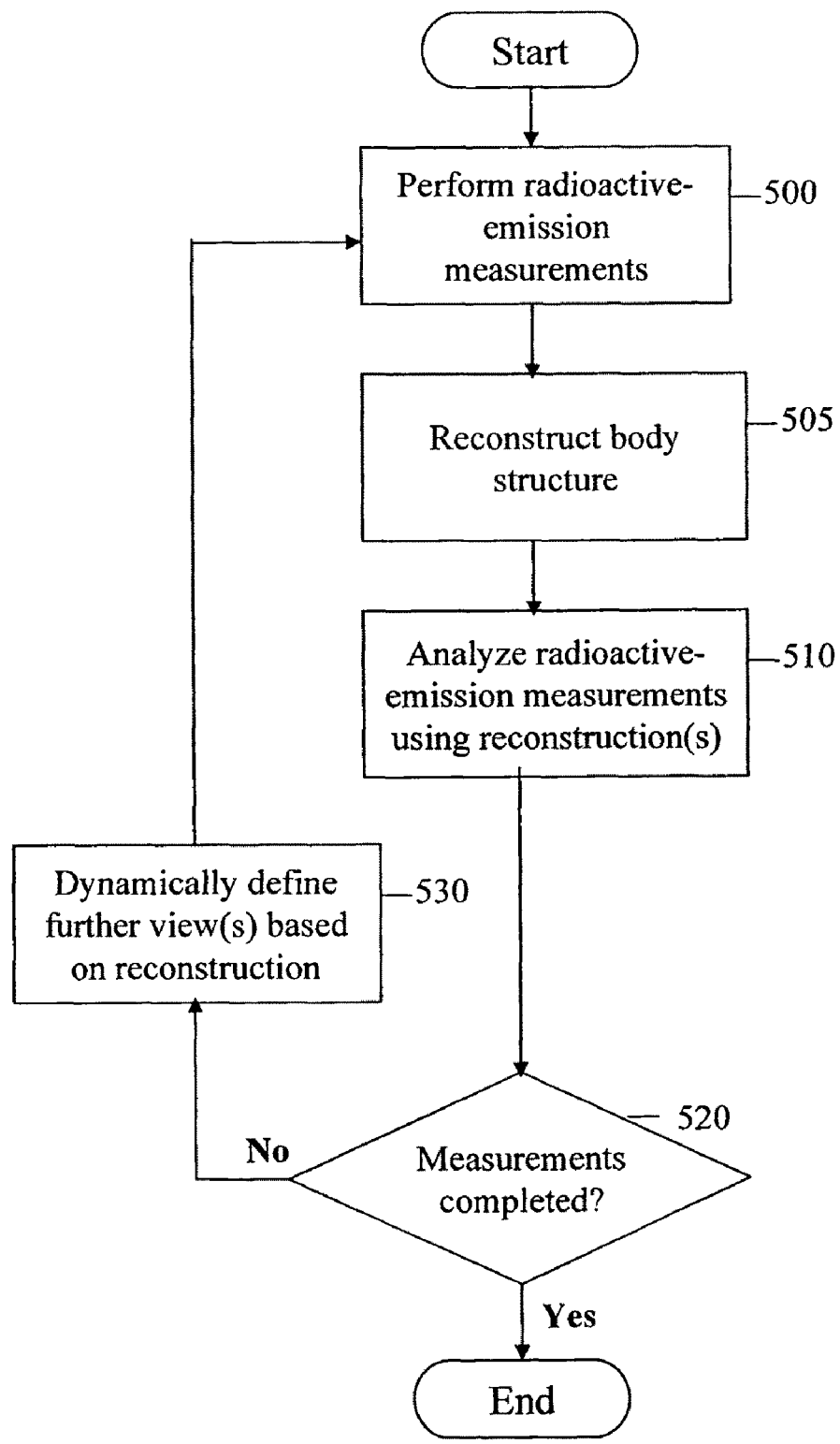

Reference is now made to FIG. 5b, which is a simplified flowchart of a iterative method of performing radioactive-emission measurements of a body structure, according to a second preferred embodiment of the present invention. In the present preferred embodiment, a reconstruction of the body structure is formed in step 505. The analysis step 510 is then performed utilizing data provided by the reconstruction(s).

Referring again to FIG. 2, preferably, analysis step 210 includes determining an accuracy of the reconstruction. Accuracy is preferably determined by analyzing the variance of the reconstructions formed over multiple iterations. Preferably, further views are defined in step 220 to concentrate on the region for which higher accuracy is required. Regions of the reconstruction having low variance provide a high degree of confidence regarding the accuracy of the reconstruction in the given region (where a portion may include the entirety of the body structure being imaged). Further views may be added to the current measurements until the variance is reduced to a required level.

Preferably, analysis step 210 includes determining a resolution of the reconstruction. Resolution is preferably determined by analyzing the full width at half maximum (FWHM) of peak values of the reconstruction. The FWHM is given by the distance between points at which the reconstructions reaches half of a peak value. Preferably, further views are defined in step 220 to concentrate on the region for which higher resolution is required.

An additional way to define future views-using the reconstruction is on an information-theoretic basis. A quality function expressing an information theoretic measure is defined. The quality function rates the information that is obtainable from the body structure when one or more permissible views are added to current measurement process. Several examples of quality functions based on information-theoretic measures are discussed in detail below. The quality function is used to rate potential further views. The measurement process may then continue at those further views whose addition to the previous views yields a high rating.

Figure 6A:
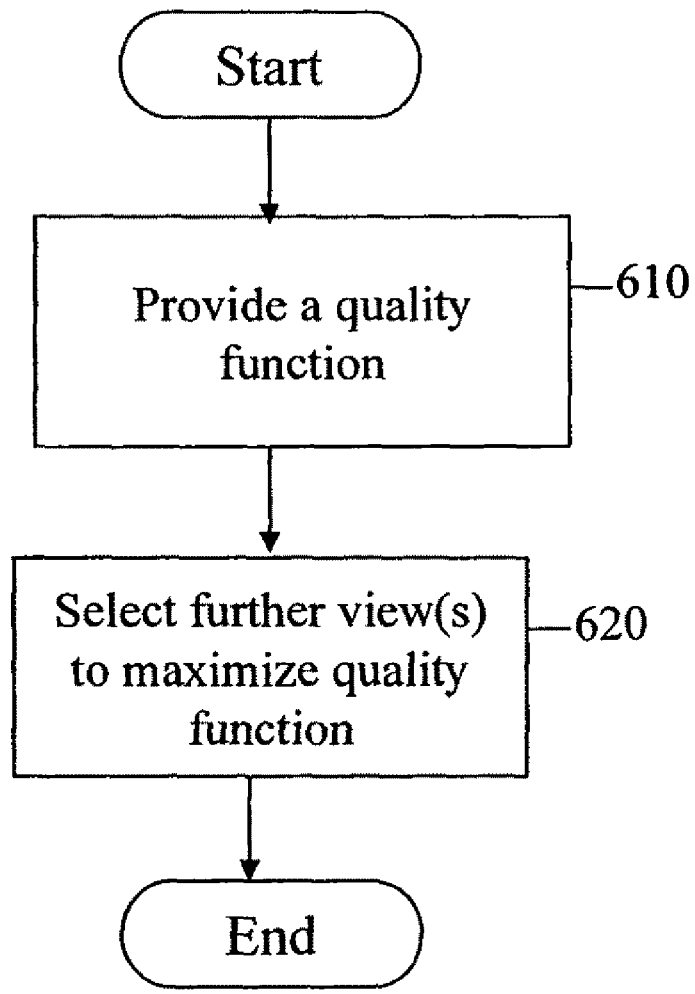
FIGS. 6a and b are simplified flowcharts of methods for dynamically defining further views, according to a first and a second preferred embodiment of the present invention.

Reference is now made to FIG. 6a, which is a simplified flowchart of a method for dynamically defining further views, according to a first preferred embodiment of the present invention. In step 610 a quality function is provided. The quality function expresses an information-theoretic measure which rates the quality of information obtainable from potential further views. In step 620 a set of further views is selected to maximize the quality function. Preferably the selected further views fulfill certain constraints; for example the further views may be selected from a predefined set or may be located in the vicinity of a region of interest within the body structure.

In the abovedescribed reconstruction-based analyses, the quality function is evaluated independently for a single reconstruction of the emission intensity of the body structure. However, quality functions may be defined which calculate the score for a given set in relation to one or more reconstructions and/or emittance models. An emittance model is a representation of a specific radioactive-emission intensity distribution within the volume U, so as to model organ targets, such as hot regions, of a radioactive emission intensity, higher than the background level, regions of low-level radioactive emission intensity, which is nonetheless above the background level, and cold regions, of a radioactive emission intensity, lower than the background level. Given an object or class of objects, emittance models may be devised to reflect expected or typical emission patterns for the given object.

Developing an emittance model for a particular body structure involves analyzing known information about the body structure to determine expected emission patterns of the body structure. In order to develop a model of a particular body structure, for example a prostate, many factors may be considered. Physical aspects, such as the size and shape of the prostate and the position of the prostate within the torso may be considered, as well as medical knowledge regarding typical emissions from healthy and diseased prostates. Additional information may concern variations between individuals, such as age, weight, percentage of body fat, and the like.

For simplicity, the following discussion describes the evaluation of information-theoretic quality functions based on emittance models only. It is to be understood that at least one of the emittance models is a reconstruction of the body structure based on past measurements. Any remaining emittance models are provided externally, and may be based on general medical knowledge or on information gathered during a previous round of emission measurements of the body structure.

Figure 6B:
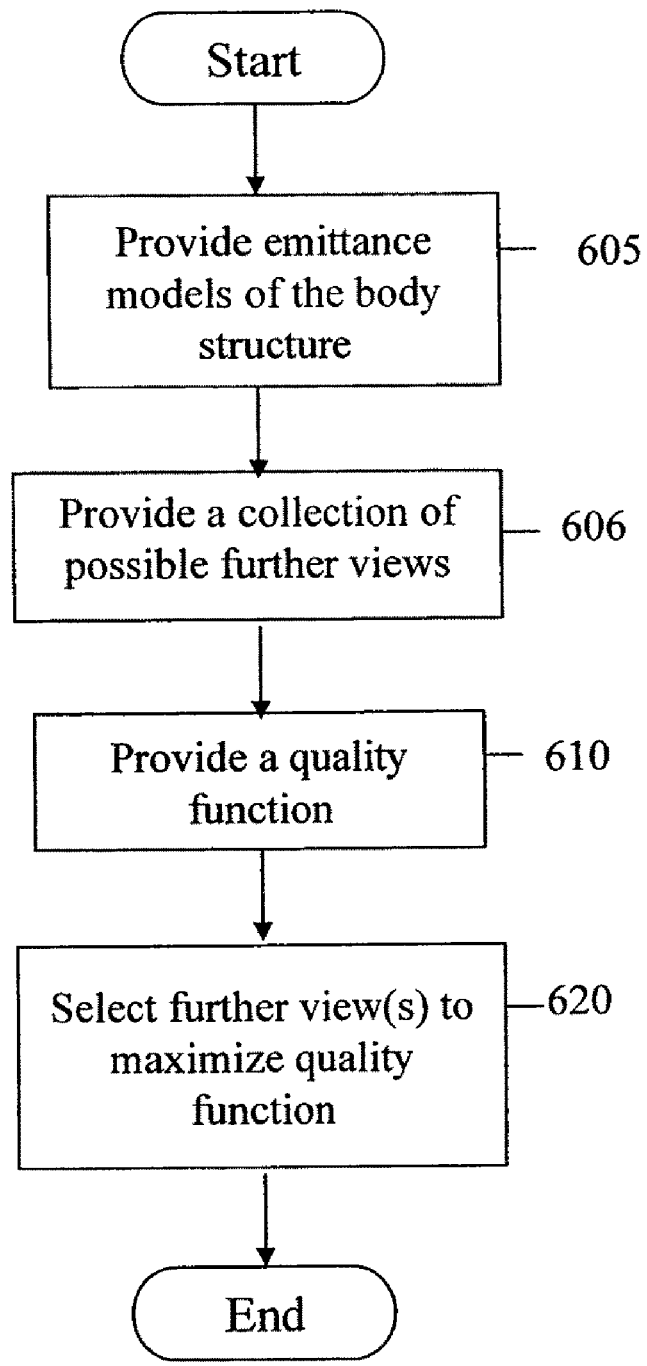

Reference is now made to FIG. 6b, which is a simplified flowchart of a method for dynamically defining further views, according to a second preferred embodiment of the present invention. The current method differs from the method of FIG. 6a by the addition of steps 605-606. In step 605 a set of one or more emittance models is provided (where the set includes one or more reconstructions of the body structure). An emittance model specifies the radiative intensity of each voxel in the body structure. As discussed above, some of the viewing parameters affect the radiative intensity of the voxels in the volume, for example the type of radiopharmaceutical and the time since administration of the radiopharmaceutical. Therefore, the emittance models provided in step 605 preferably correspond to the relevant viewing parameters. In step 606 a collection of possible further views of the body structure is provided. The collection of views includes possible further views for future measurements, preferably based on anatomical and other constraints. Furthermore, the quality function provided in step 610 may utilize multiple emission models.

Figures 7A, 7B:
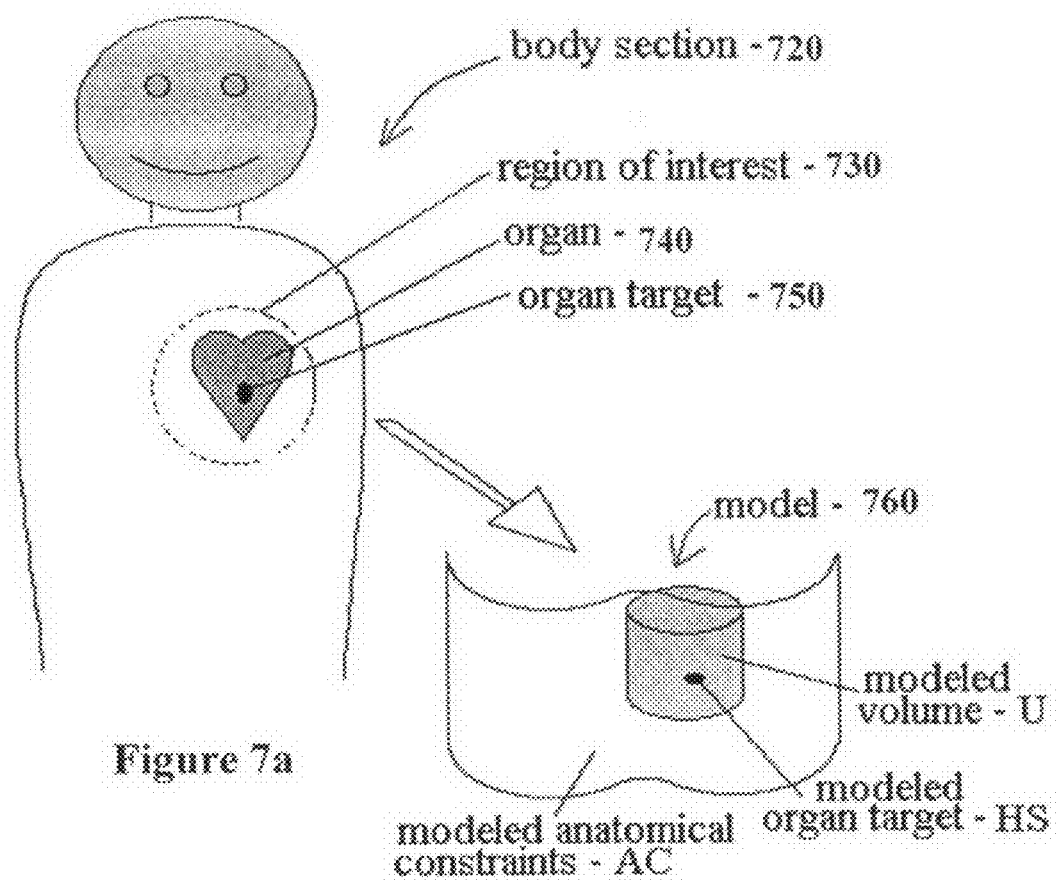
FIGS. 7a and 7b present the principles of modeling, for obtaining an optimal set of views, in accordance with the present invention.

Reference is now made to FIGS. 7a and 7b which present the principles of modeling of a body structure, in accordance with the present invention. FIG. 7a schematically illustrates a body section 720, having a region of interest (ROI) 730. The region of interest 730 is associated with a body structure 740, with a specific radioactive-emission-density distribution, possibly suggestive of a pathological feature 750, termed herein an organ target 750. Additionally, there may be certain physical viewing constraints, associated with the region of interest 730. Model 760, as illustrated in FIG. 7b, represents body section 720 as a collection of voxels, having a specified radioactive-emission intensity distribution.

It will be appreciated that the model 760 of the region of interest 730 may be based on general medical information of the body structure 740 and common pathological features associated with it. Additionally, the model may be based on information related to a specific patient, such as age, sex, weight, and body type. Furthermore, a structural image, such as by ultrasound or MRI, may be used for providing information about the size and location of the body structure 740 in relation to the body section 720, for generating the model 760.

Figure 8:
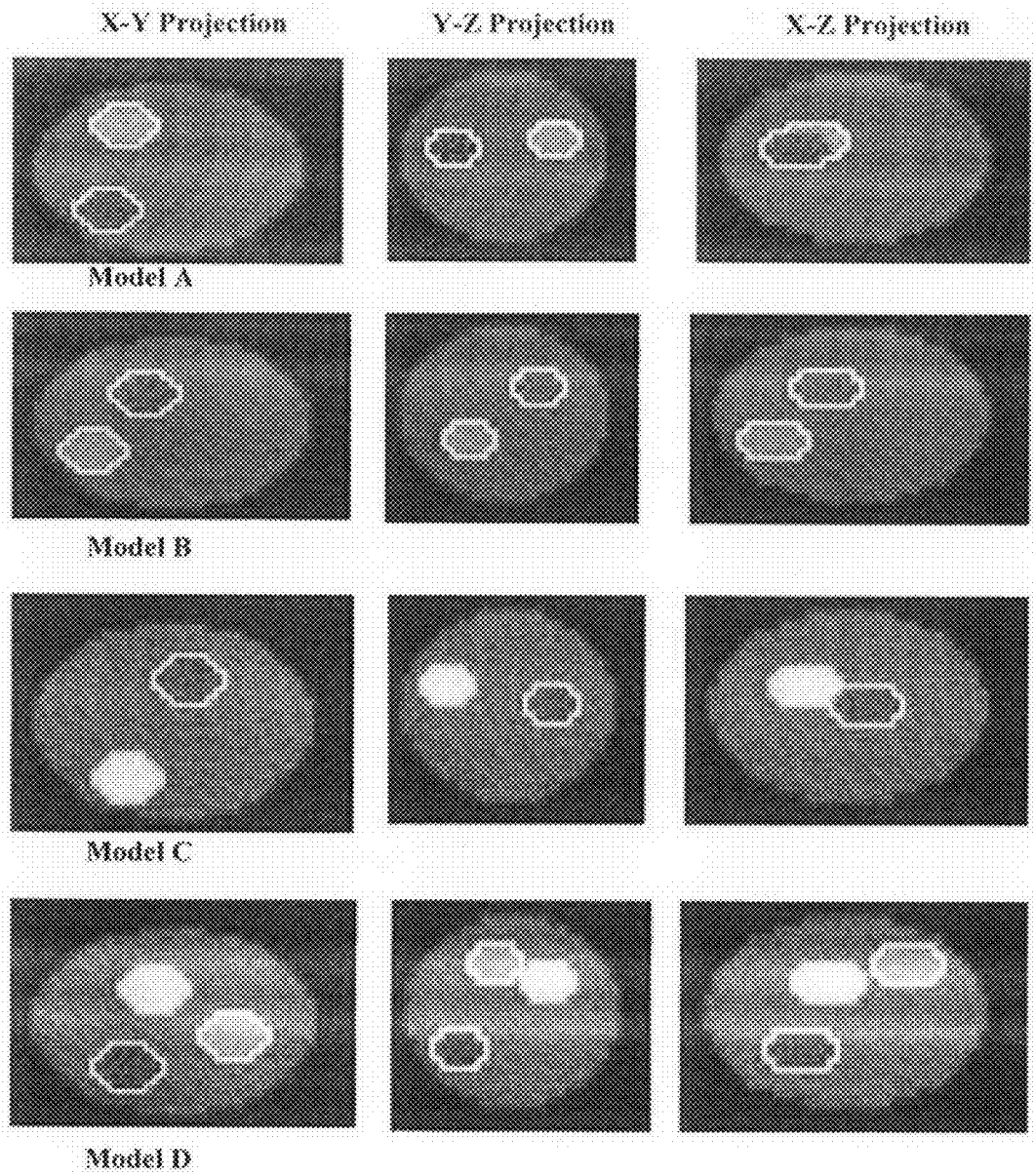
FIG. 8 shows four models of a prostate emittance model.

Reference is now made to FIG. 8, which shows four models of a prostate emittance model. Three views are given for each of the emittance models shown.

In a first preferred embodiment, the quality function implements a separability criterion. Separability is a measure of the extent to which the measurements that are obtained from each pair of models can be distinguished from one another.

Figure 9A:
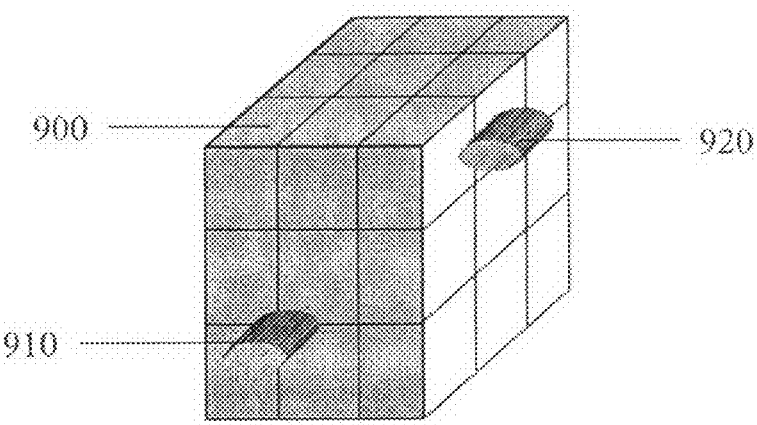
FIGS. 9a-9f show emittance models of a given volume to illustrate view selection using the separability criterion.
Figure 9B:
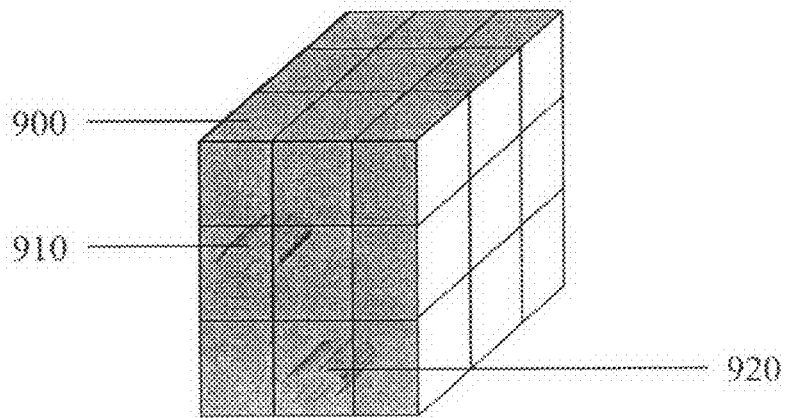
Figure 9C:
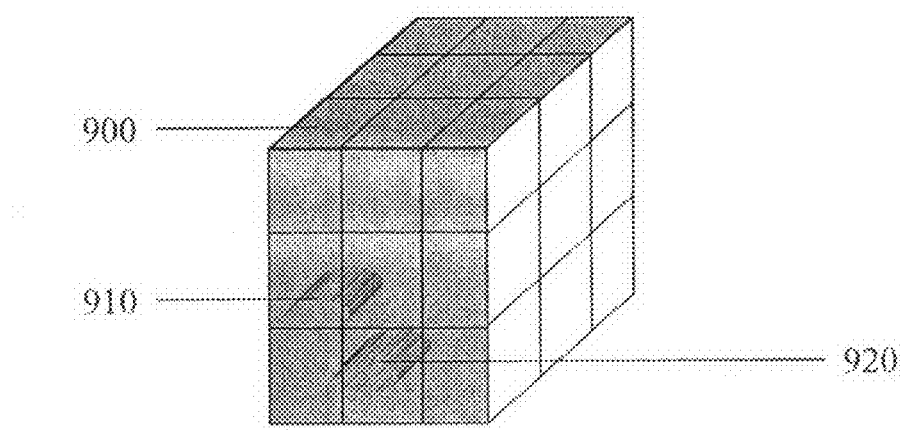
Figure 9D:
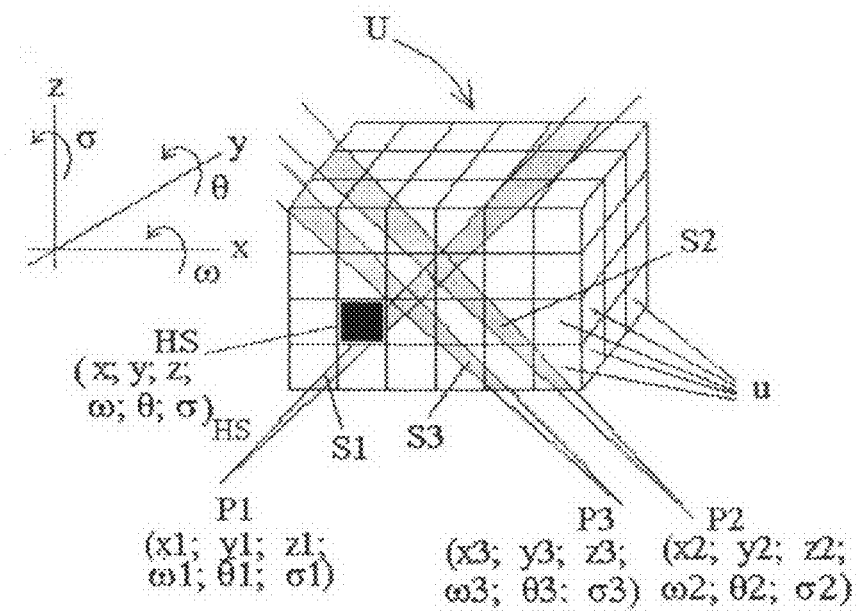
Figure 9E:
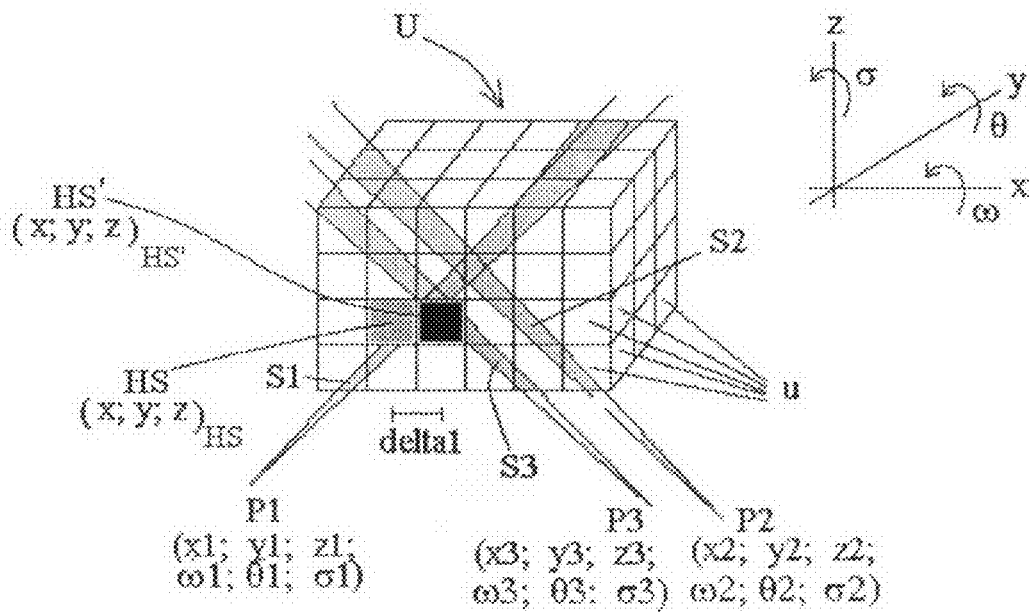
Figure 9F:
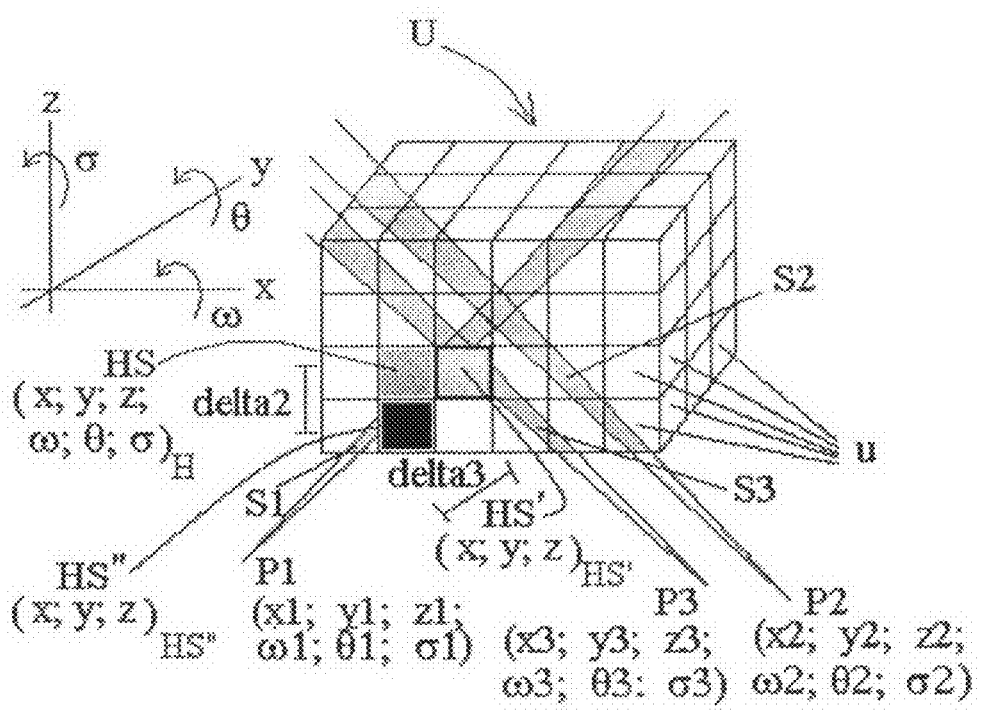

The concept of separability is illustrated in FIGS. 9a-9c, each of which shows an emittance model of a given volume 900. Each of the emittance models contains two high-emittance portions (hot regions), 910 and 920, which are located in respectively different locations in each of the models. It can be seen that the hot regions in emittance models 9b and 9c are in similar portions of the volume, as opposed to the hot regions in model 9a. It may therefore be difficult to distinguish between reconstructions of emittance models 9b and 9c. The separability criterion ensures that the selected set includes views which provide reconstructions which distinguish between emittance models 9b and 9c.

Letting I be the emittance model set, a measure for the dissimilarity of any two given densities in I is defined. Since most state-of-the-art estimating algorithm are aimed at finding ML estimators, in the current example the quality function is based on the likelihood function. The likelihood of an estimator of I, given a set of Poissonian measurements y is:

$$L(I) = \sum_t \left\{ -\sum_u \phi_t(u)I(u) + y_t \ln \sum_u \phi_t(u)I(u) - \ln(y_t!) \right\} \quad (19)$$

For separability, it is desired that this measure be different for each I∈I. Since the measure is a random variable that depends on the actual measurements, all possible pairings of emittance models should be examined to ensure that the resulting distributions are separable. A quality function that captures this separability is given by the square of the difference between the means of the distributions normalized by the sum of their variances:

$$SEPARABILITY_\Phi(I_1, I_2) = \frac{|EL(I_1) - EL(I_2)|^2}{\mathrm{Var}L(I_1) + \mathrm{Var}L(I_2)} \quad (20)$$

The expectations and variances in Equation 20 are taken over random measurements y, sampled from the true intensity $I_1$ (note that the measure is not symmetric).

Since the true (unknown) intensity can be any I∈I, a projection set Φ* that maximizes the worst-case separability is desired. That is:

$$\Phi^* = \arg\max_\Phi \min_{I_1, I_2 \in I} SEPARABILITY_\Phi(I_1, I_2) \quad (21)$$

Scoring for separability is based on the minimum separability obtained with a given set of views for all of the possible pairings of emittance models from the set of emittance models, thereby enabling defining a desired resolution in more than one direction, or in more than one portion of the volume. All of the emittance models are modeled on a substantially identical volume. The emittance models preferably differ from one another in the modeled organ targets, where the modeled organ targets are separated by a difference of at least the required resolution (where the displacement which produces the required resolution is denoted delta herein). Substantially identical sets of views are formed from the collection of views, and each of the formed sets is scored with respect to each of the pairs. One of the sets of views is selected, based on the minimum or average score for the plurality of pairs.

For example, assume the set of emittance models contains the three models 9a-9c. A separability score is calculated for a given formed set of views by applying Equation 20 to all three pairs 9a/9b, 9a/9c, and 9b/9c. The lowest of the three calculated values is taken as the separability score for the formed set. Once a separability score has been calculated in such manner for each of the formed sets of views, the view set having the highest separability is selected.

The separability criterion may be used to ensure that a required resolution is obtained in all or a portion of the body. In a preferred embodiment, view set selection for separability is performed utilizing a set of emittance models consisting of one pair of emittance models having substantially identical volumes but with different modeled organ targets. The modeled organ targets are separated by a delta in a given direction so as to define a required resolution in that direction and portion of the volume U. Substantially identical sets of views are formed from the collection of $$\Phi^* = \mathrm{argmax}_\phi \sum_{I \in I} \sum_{u \in U} [F_\Phi(I)]_{u,u} \quad (23)$$

Alternately, a set may be chosen to minimize the inverse of the Fisher information, by selecting for:

$$\Phi^* = \mathrm{argmin}_\phi \sum_{I \in I} \sum_{u \in U} \lfloor F_\Phi(I)^{-1} \rfloor_{u,u} \quad (24)$$

Since inverting $F_\Phi(I)$ may be computationally expensive, the $\lfloor F_\Phi(I)^{-1} \rfloor_{u,u}$ term in Equation 24 may be replaced with $1/[F_\Phi(I)]_{u,u}$ (thus neglecting the off-diagonal elements of the Fisher Information matrix $F_\Phi(I)$). Note that Equations 23 and 24 are not mathematically equivalent, and may therefore yield different selected sets.

In the preferred embodiment, evaluating the quality function is performed using the reliability criterion, and two or more emittance models are provided, having substantially identical volumes, but different modeled organ targets. Substantially identical sets of views are formed for all the emittance models, and each set is scored for reliability. One of the sets of views is then selected based on the average score for all the of the emittance models.

Figure 9G:
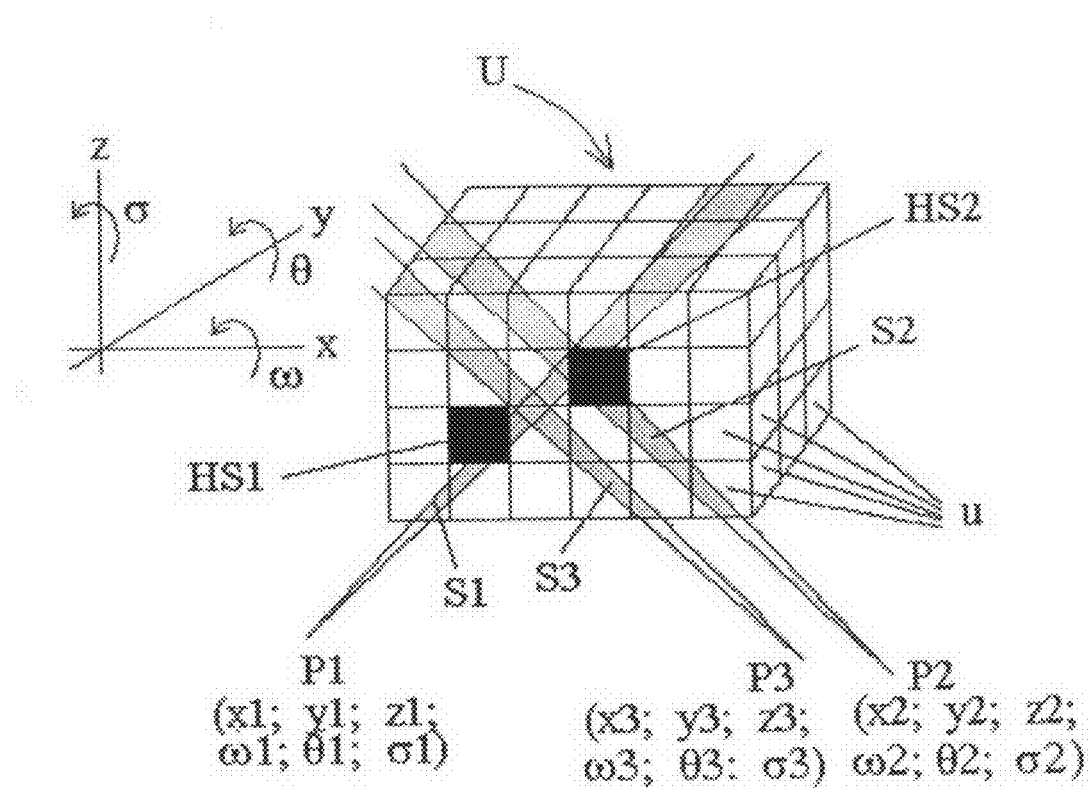
FIGS. 9g-9i show emittance models of a given volume to illustrate view selection using a weighted-combination criterion.
Figure 9H:
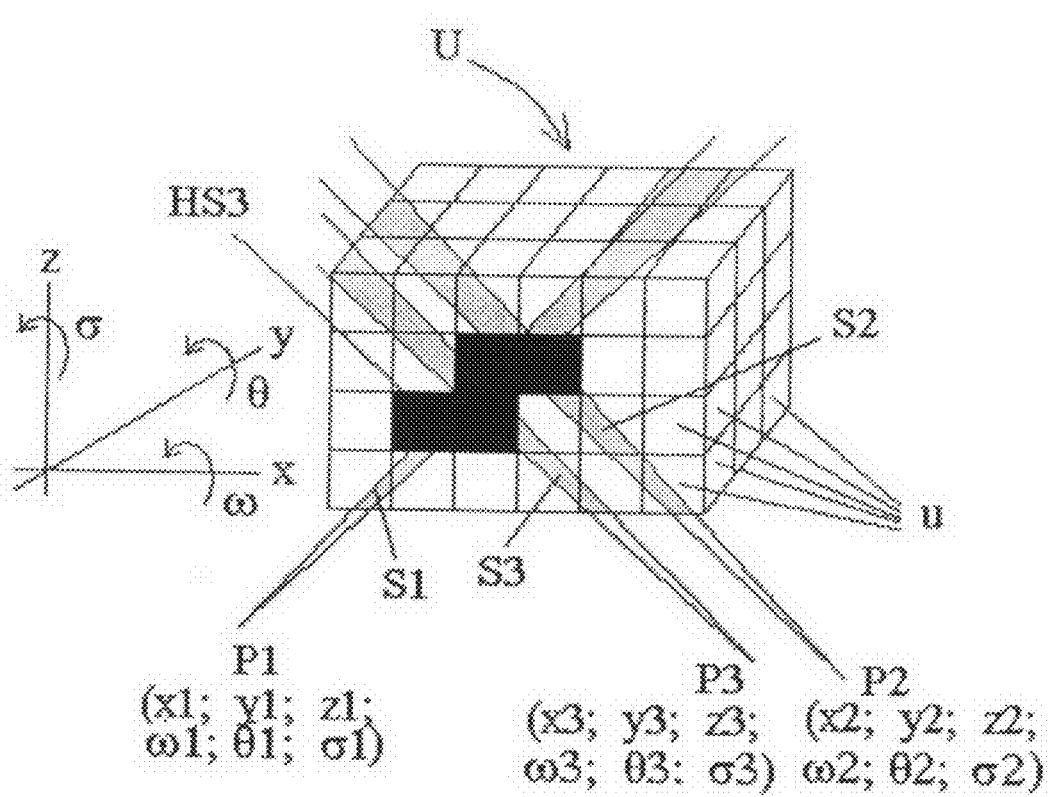
Figure 9I:
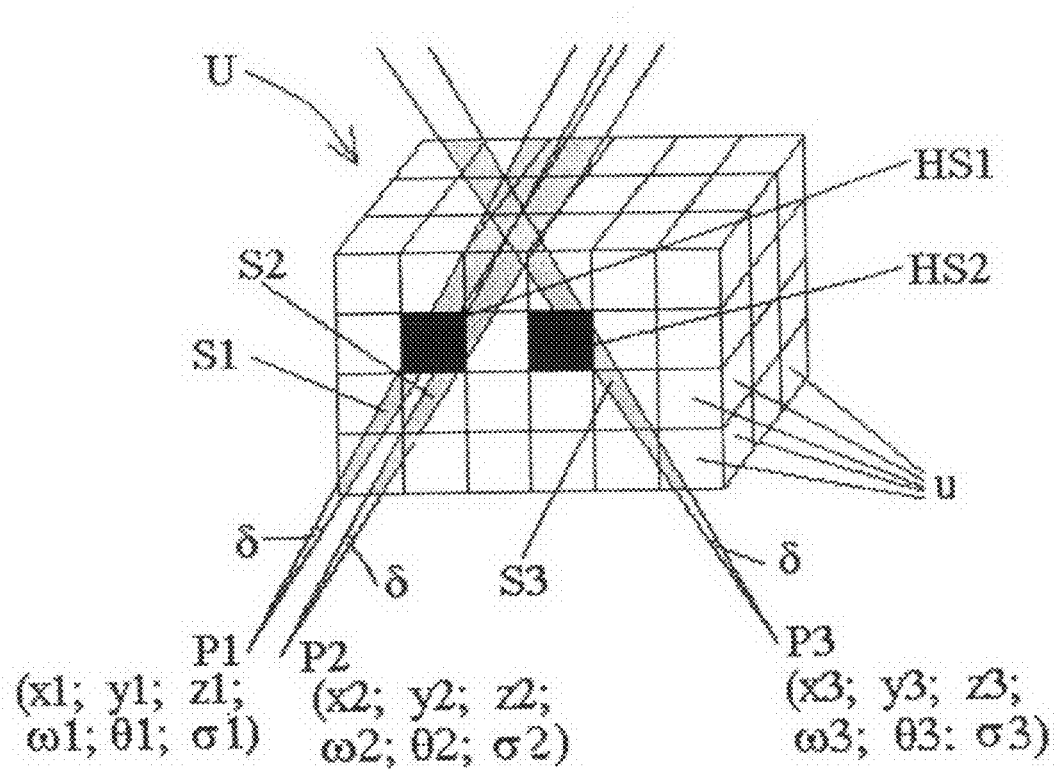

In a further preferred embodiment, a weighted combination of several information theoretic measures is used. For example, a plurality of models may be provided, all having substantially identical dimensions and volumes, as follows:

i. a pair of models with slightly different distributions of radioactive emission sources, as seen in FIGS. 9g and 9h, for scoring sets of views in terms of separability;

ii. a model with a given distribution of radioactive emission sources, as seen in any one of FIG. 9g, 9h or 9i, for scoring sets of views in terms of reliability.

Identical sets of views may be applied to all the models, and each view may be scored in terms of separability and reliability. An optimal set of views may be selected based on a summation of the two scores, or based on a weighted average of the two scores, where the relative weight given to each criterion reflects the relative importance of each measure per the given application.

The quality function is preferably defined in accordance with one of the following: worst case effectiveness for the given further view over the volume, views and of the required set may be large, a brute force scheme might not be computationally feasible.

In an additional preferred embodiment, a so-called "greedy algorithm" is used to incrementally construct larger and larger sets, until the required number of further views is defined. When multiple further views are required, it is computationally complex to maximize the quality function over all possible combinations of further views. The greedy algorithm reduces the computational burden by selecting the further views one at a time. The algorithm starts with a current set of views, and for each iteration determines a single view that yields the maximum improvement of the set score (hence the name "greedy").

In theoretical terms, assume $\rho(\cdot)$ is the quality measure we are using for the view selection, and assume without loss of generality that we are trying to maximize this measure. We gradually build a set W of projections as follows. We start with an empty set $W=\emptyset$, and at every stage choose the projection that maximizes the quality measure when added to the current set:

$$W \leftarrow \mathrm{argmax}_{W'}\{\rho(W') | W' = W \cup \{\phi\}, \phi \in \Phi\} \quad (27)$$

In other words, during a given iteration, a respective score is calculated for a combination of the previous set with each of the views which is not a member of the current set. The current set is then expanded by adding the view which yielded the highest respective score, and the expanded current set serves as the input to the following iteration. Thus the number of times the scoring function is calculated per iteration drops from iteration to iteration. For a large collection of possible views, the greedy algorithm reduces the total number of computations required for set selection.

Figure 10:
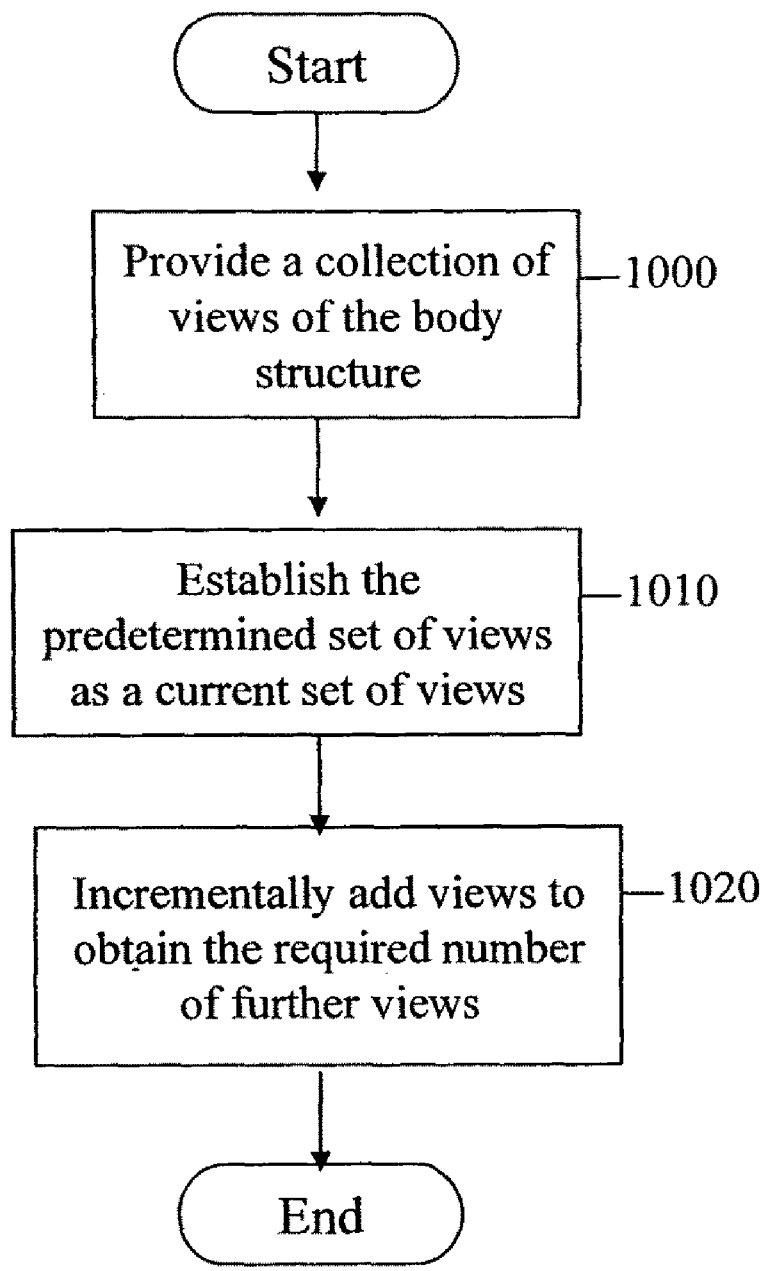
FIG. 10 is a simplified flowchart of an iterative method for selecting further views, according to a preferred embodiment of the present invention.

Reference is now made to FIG. 10, which is a simplified flowchart of an iterative "greedy" method for defining further views, according to a preferred embodiment of the present invention. In step 1000 a collection of views of the body structure is provided. The collection of views includes possible further views for future measurements, preferably based on anatomical and other constraints. In step 1010, the set of views used for the previous emission measurements is established as a current set of views. In step 1020 the view set is incrementally increased by a single further view during each iteration, until the required number of further views has been selected.

Figure 11:
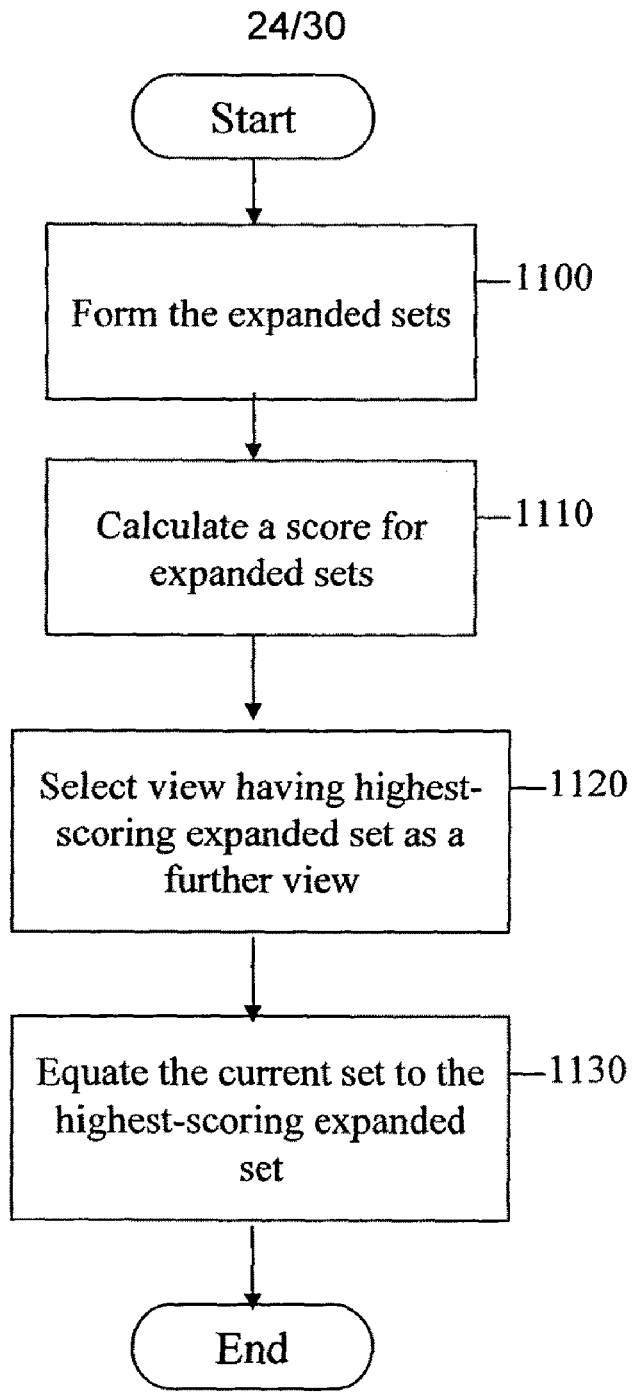
FIG. 11 is a simplified flowchart of a single iteration of a view selection method, according to a preferred embodiment of the present invention.

Reference is now made to FIG. 11, which is a simplified flowchart of a single iteration of the view selection method of FIG. 10, according to a preferred embodiment of the present invention. The method of FIG. 11 expands the current set of views by a single view. The method begins with a current set of views, which is the predetermined set (step 1010 above) for the first iteration of the greedy algorithm, or the set formed at the end of the previous iteration (step 1120 below) for all subsequent iterations. In step 1100, a respective expanded set is formed for each view not yet in the current set of views. A given view's expanded set contains all the views of the current set of views as well as the given view. In step 1110, a respective score is calculated for each of the expanded sets using the quality function. In step 1120, the view which yielded the highest-scoring expanded set is selected as a further view, to be used for further radioactive emission measurements. Finally, in step 1130, the current set is equated to the highest-scoring expanded set by adding the selected view to the current set. The newly formed current set serves as an input to the subsequent iteration, until the desired number of views is attained.

Figure 12:
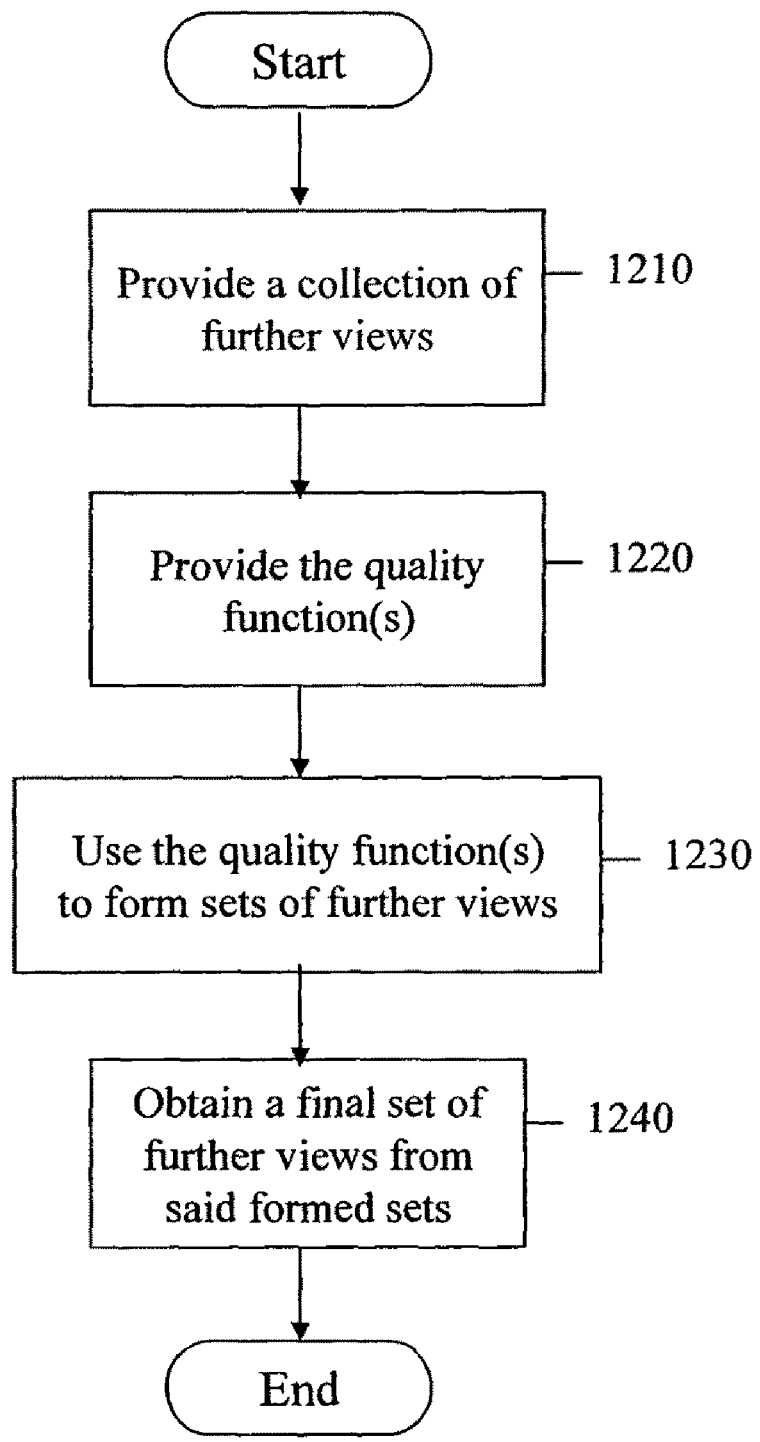
FIG. 12 is a simplified flowchart of a method for dynamically defining further views, according to a third preferred embodiment of the present invention.
Figure 13:
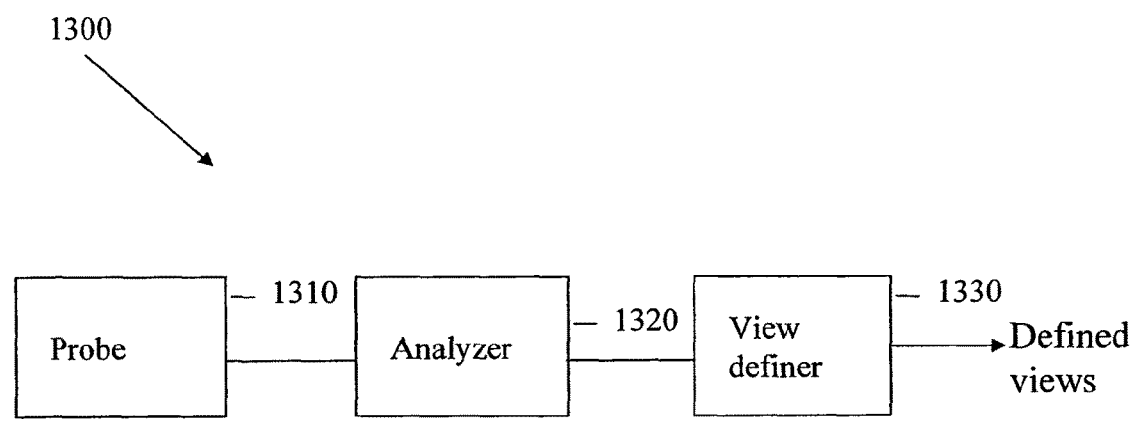
FIG. 13 is a simplified block diagram of measurement unit for performing radioactive-emission measurements of a body structure, according to a preferred embodiment of the present invention.

Reference is now made to FIG. 12, which is a simplified flowchart of a method for dynamically defining further views, according to a third preferred embodiment of the present invention. In step 1210, a collection of possible further views for performing radioactive-emission measurements of the body structure is provided. Each of the views is associated with at least one viewing parameter. Preferably the viewing parameters consist of at least one the following: detector unit location, detector unit orientation, collection angle, and measurement duration.

In step 1220 at least one quality function is provided. Each quality function is for evaluating sets of views, essentially as described above. A single quality function may be used to select several sets of views, where each set of views contains a different number of views.

In step 1230, multiple sets of further views (where a set may include a single further view) are formed from the collection of views, using the quality function(s) provided in step 1220. In a first preferred embodiment, each of the sets is formed using a different one of the quality functions. In an alternate preferred embodiment, emission measurements obtained from probe 1310. View definer 1330 dynamically defines further views for measurements, based on the analysis provided by analysis unit 1320. The analysis and view definition are performed substantially as described above.

The abovedescribed methods for radioactive-emission measurements of a body structure begin by performing measurements at a predetermined set of views. The results of the initial measurements are then analyzed and further views are defined.

The initial set of views is preferably selected based on information theoretic measures that quantify the quality of the data fed to the reconstruction algorithm, in order to obtain the best data for reconstructing a three-dimensional image of the body structure.

In accordance with the present invention, our approach is delineated by the following process:
i. modeling the body structure or region of interest as a model of a volume U, possibly with one or several modeled organ targets HS, within anatomical constraints AC (see FIGS. 7a-7b);
ii. obtaining an optimal and permissible initial set of views for the modeled volume U; and
iii. initiating the radioactive-emission measurements at the optimal set of views.

The following section concentrates on the second step of the process, namely, obtaining the optimal and permissible set of initial views for performing the radioactive-emission measurements of the body structure. The initial predetermined set of views is denoted herein the optimal set of views.

We consider here the following problem: Assume that there is a large pool of candidate views to choose from, but due to time restrictions or other restrictions we are limited to a specific number of views N. Which are the best N projections in terms of the quality of the reconstruction? It is further assumed that the pool of projections may be constrained, and hence general sampling theorems (e.g., Radon Transform) cannot be applied. For instance, we consider a scenario in emission tomography where the detecting unit can be located on top of one face of a given volume but not on the others. In such cases, methods such as EM estimation do not clearly establish parameters, in the case shown a location (in the XYZ coordinate system), orientation (e), 0 and a) and collection angle $\delta$. The viewing parameters determine which voxels in volume 1500 are within a detecting unit's collection angle, and generally affect the probability of detection for each voxel. The probability of detection may be affected by additional factors, including the attenuation coefficients within the volume.

During data collection, the probability of detection for each voxel is dependent on the parameters outlined above. In the preferred embodiment, a respective projection is calculated for each view, giving the view's detection probability distribution (i.e. the detection probability for each voxel of the volume). For a given view, the associated projection will have significant detection probabilities only for those voxels within the sector defined by the detecting unit's collection angle and location and orientation, as illustrated in conjunction with FIG. 1*j*.

The detection probability distribution for each view, that is the group of probabilities for each voxel, for a given view, is calculated according to techniques known in the art for determining the detection probability of a radioactive emission from a given voxel, under the constraints specified by the viewing parameters, for example, based on computer simulations of the geometry and the other viewing parameters, delineated hereinabove.

Generally, more distant voxels will have a lower probability of detection than closer voxels along the same line of sight. The volume attenuation coefficient may be constant or may vary over the volume. Thus, different sets of views may be produced for a single sector, by defining volumes with differing attenuation coefficients. For example, bone tissue and muscle tissue have different attenuations. Anatomical knowledge of the body structure being imaged may be used to develop a model of the volume U with a non-uniform attenuation that reflects the expected attenuation of the given body structure.

Figure 14:
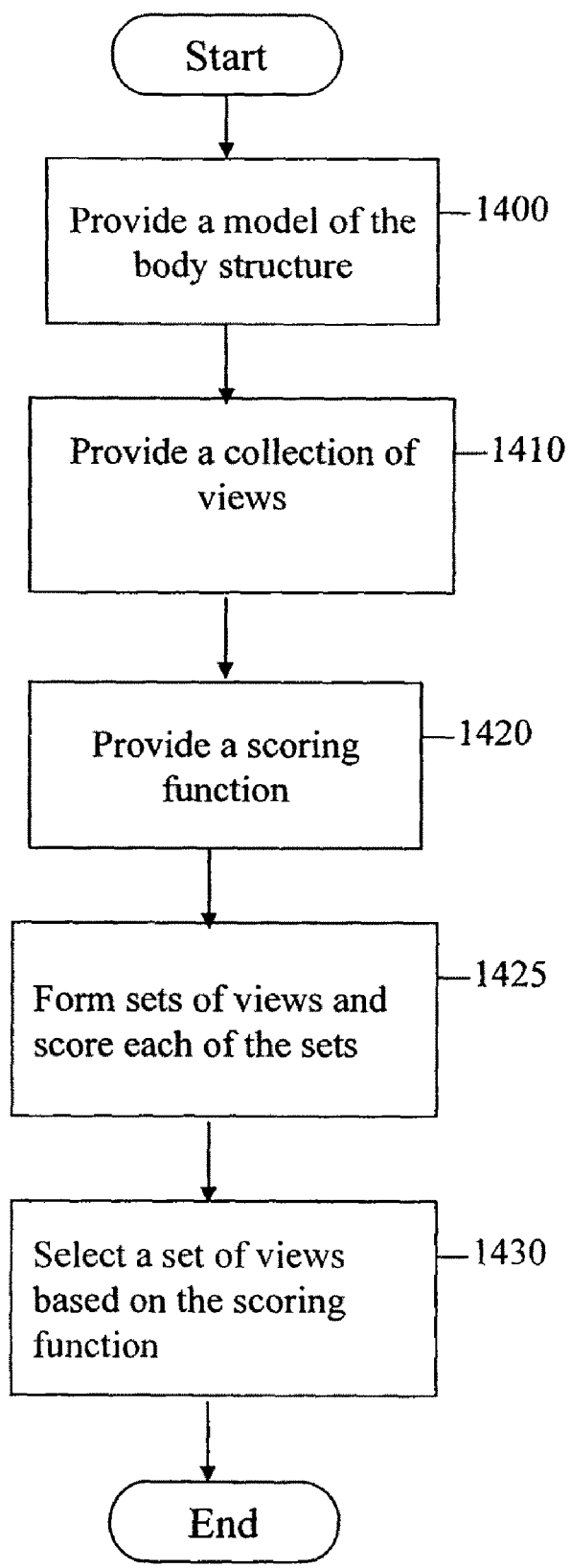
FIG. 14 is a simplified flowchart of a method for selecting an optimal initial predetermined set of views of a volume to be imaged, according to a preferred embodiment of the present invention.
Figure 15:
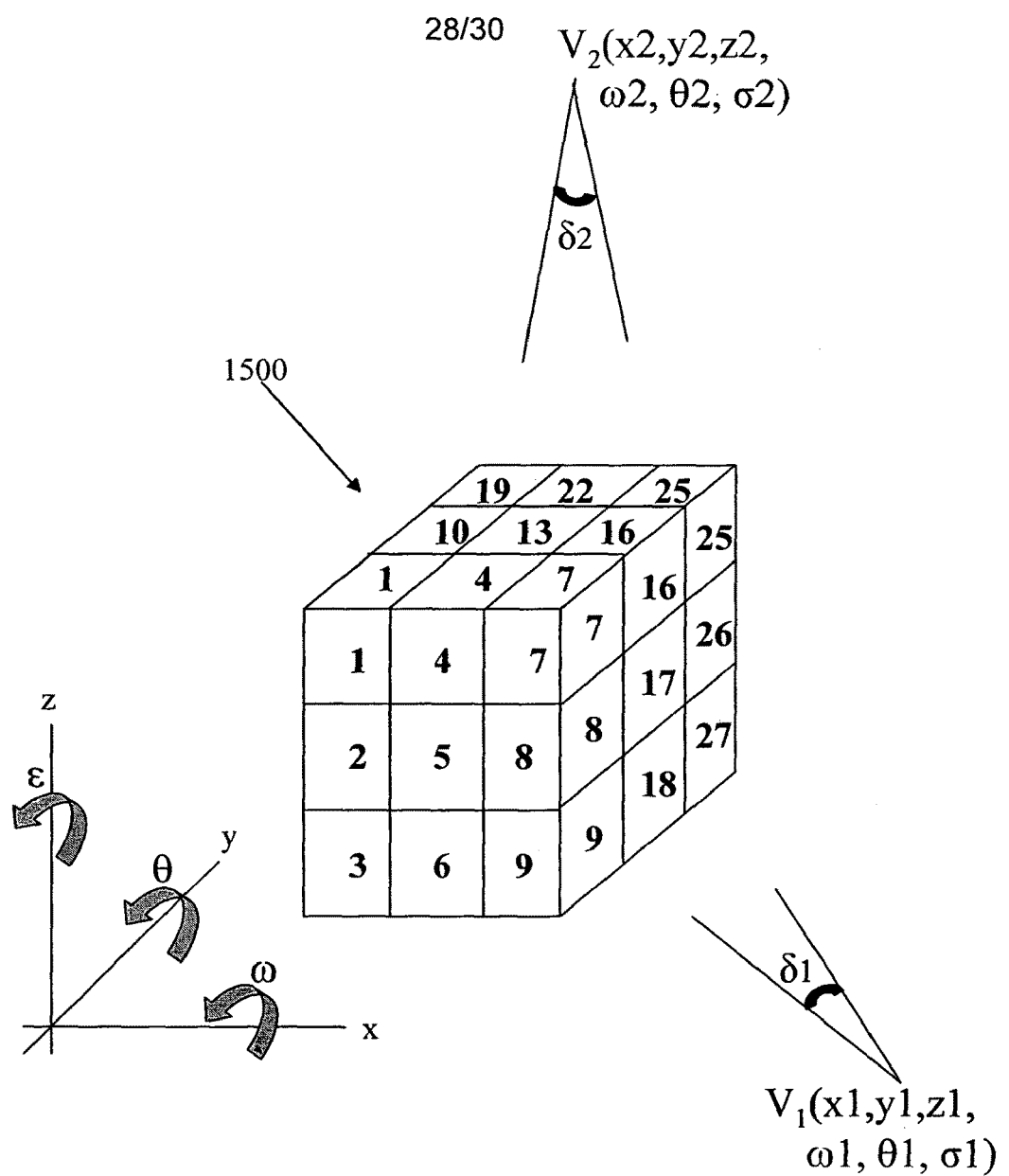
FIG. 15 shows an example of a volume with two views.

Referring again to FIG. 14, in step 1420 a scoring function is provided. The scoring function rates the information that is obtainable from the volume using any set of views (containing at least one view) taken from the collection of views. Evaluation of the scoring function does not require data from previously performed measurements. This is in contrast to the quality function, which rates the information quality on the basis of previous emission measurements as well as by the characteristics of possible further views. Preferably, the scoring function is a function of the detection probability distribution, as given by the projections. Several preferred embodiments of the scoring function, are discussed in detail below.

In step 1425, sets of views are formed from the collection of views. A score is then calculated for each of the sets.

In step 1430, the scores calculated in step 1425 are used to select one of the formed sets of views as the optimal set of views for the abovedescribed methods of performing radioactive-emission measurements of a body structure. A given scoring function may be used to select a set in a number of ways. In a first preferred embodiment, a required number of views is specified, and the highest scoring set with the specified number of views is selected. In a second preferred embodiment, the user may specify a minimal score which is known to provide satisfactory information quality, and select the smallest set which provides the specified score. However given a large collection of views the required number of calculations may be prohibitive. A third preferred embodiment used to reduce the computational burden is the greedy algorithm embodiment, similar to the abovedescribed method of FIGS. 10-11.

As discussed above, the scoring function is a measure of the quality of information which may be gathered for the volume using the given set of views. Both the separability and reliability criteria discussed above may be utilized as scoring functions, substantially as described above.

In an additional preferred embodiment, the scoring function implements a uniformity criterion, to ensure uniform coverage of the volume. It is often desired to obtain a uniform reconstruction quality among a given set of voxels $W \subset U$, where W is the set of voxels for which it is desired to obtain uniform detection. Note that by selecting the appropriate W, the uniformity criterion is applied to all or a portion of the body. The uniformity criterion ensures that the spread of the total influence of each element on the set of measurements is as uniform as possible. The uniformity criterion depends only on the collection of views Φ and requires no assumptions on the distribution I.

For a set Φ of projections, the total influence of an element, u, is given by $\Sigma_{\phi \in \Phi}\phi(u)$. Normalizing these values to $P_\Phi(u)$, such that $$\sum_{u \in W} P_\Phi(u) = 1,$$

a probability measure is obtained for which the entropy H(Φ) can serve as a uniformity measure:

$$H(\Phi) = -\sum_{u \in W} P_\Phi \log P_\Phi(u) \tag{28}$$

The selected set Φ* is the set (containing the required number of views) that satisfies:

$$\Phi^* = \arg\max_\Phi H(\Phi) \tag{29}$$

Figure 16:
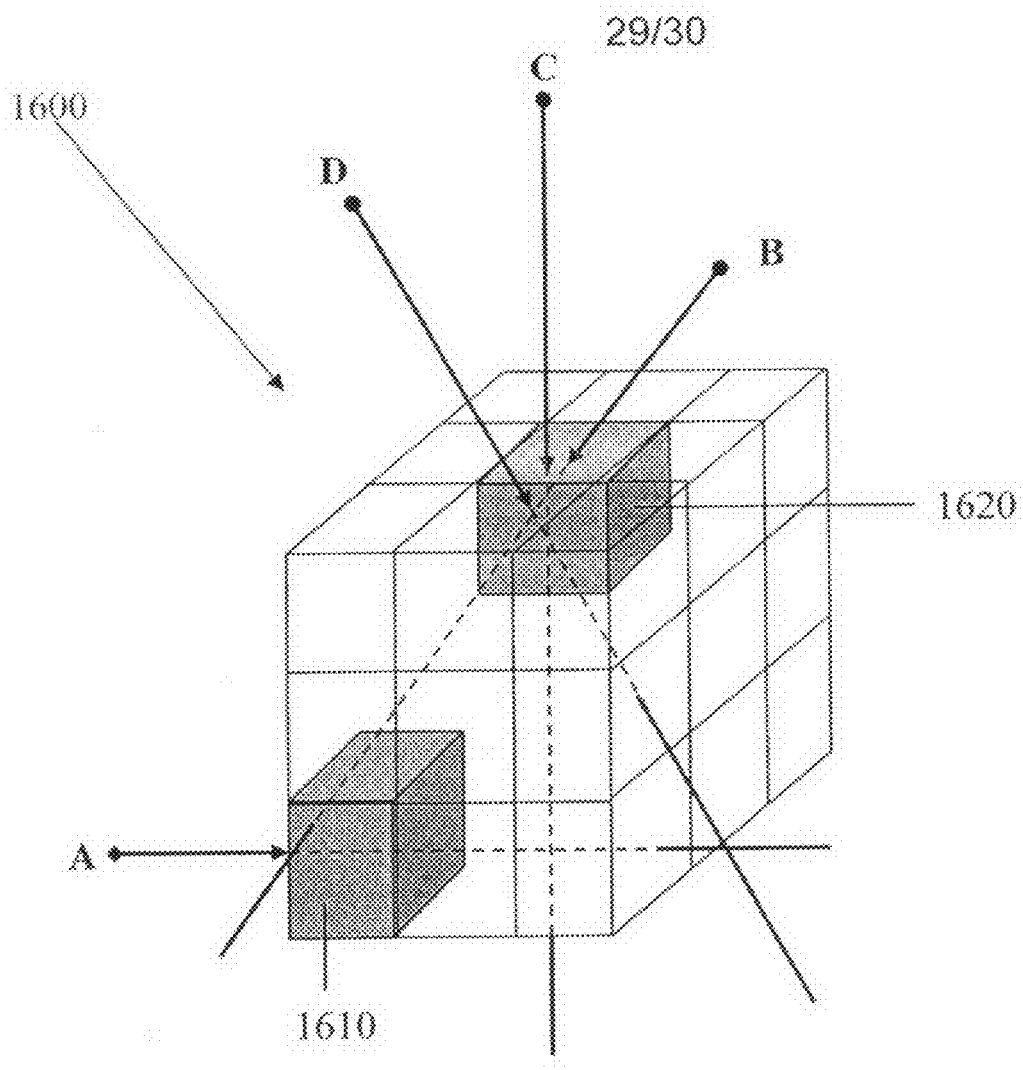
FIG. 16 illustrates the concept of uniform coverage of a volume.

Reference is now made to FIG. 16, which illustrates the concept of uniform coverage of a volume. Volume 1600 consists of twenty-seven cube-shaped voxels, including voxels 1610 and 1620. A, B, C and D are three views of volume 1600, showing the detector position and orientation for each view. For the uniformity criterion, it is desired that the overall influence of voxels 1610 and 1620 be approximately equal.

Assume that the probabilities of detection are as follows:

| View | Voxel 1610 | Voxel 1620 |
|------|------------|------------|
| A    | 0.6        | 0          |
| B    | 0.2        | 0.5        |
| C    | 0          | 0.3        |
| D    | 0          | 0.1        |

Consider two possible sets of views: set {A, B, C} and set {B, C, D}. For set {A, B, C}, the total contribution of voxel 1610 is 0.8 (0.6+0.2+0) and of voxel 1620 is 0.8 (0+0.5+0.3). Normalizing these values for set {A, B, C} gives a probability set of [0.5,0.5]. For set {B, C, D}, the total contribution of voxel 1610 is 0.2 (0.2+0+0) and of voxel 1620 is 0.9 (0.5+0.3+0.1). Normalizing these values for set for set {B, C, D} gives a probability set of [0.18,0.82]. Thus:

$$H(\{A,B,C\}) = -(0.5*\log_2 0.5 + 0.5*\log_2 0.5) - (-0.5 - 0.5) = 1$$

$$H(\{B,C,D\}) = -(0.18*\log_2 0.18 + 0.82*\log_2 0.82) = -(-0.44 - 0.07) = 0.51$$

Set {A, B, C} is thus seen to provide a more uniform coverage of volume 1600 than set {B, C, D}.

In an additional preferred embodiment, the greedy algorithm is used to incrementally construct larger and larger sets, until a set containing the required number of views is obtained. As described for FIGS. 10-11 above, the algorithm starts with an initial set of views (which may be the empty set), and in each iteration adds the view that yields the maximum improvement of the set score, until the required optimal set of views is obtained.

In a further preferred embodiment of a method for the selection of an optimal set, multiple view sets are first formed from one or more scoring functions, and then a final selection is made of one of the resulting sets, substantially as described for FIG. 12 above. Preferably the viewing parameters consist of at least one the following: detector location, detector orientation, viewing angle, material, thickness, collimator length, septa thickness, cell size, detection duration, time of detection, and a type of radiopharmaceutical. Knowledge about the conditions under which a particular set of measurements will be taken may be used to determine the optimal final set of views for a given data collection scenario.

The abovedescribed methods may each be embodied as a computer program stored on a computer-readable storage medium. In the preferred embodiment, computer-readable storage medium contains a set of instructions for defining views for radioactive-emission measurements of the body structure. An analysis routine analyzes the radioactive-emission measurements obtained from a radioactive-emission-measuring probe, and a view definition routine dynamically defines further views for measurements, based on the analyzing.

Figure 17:
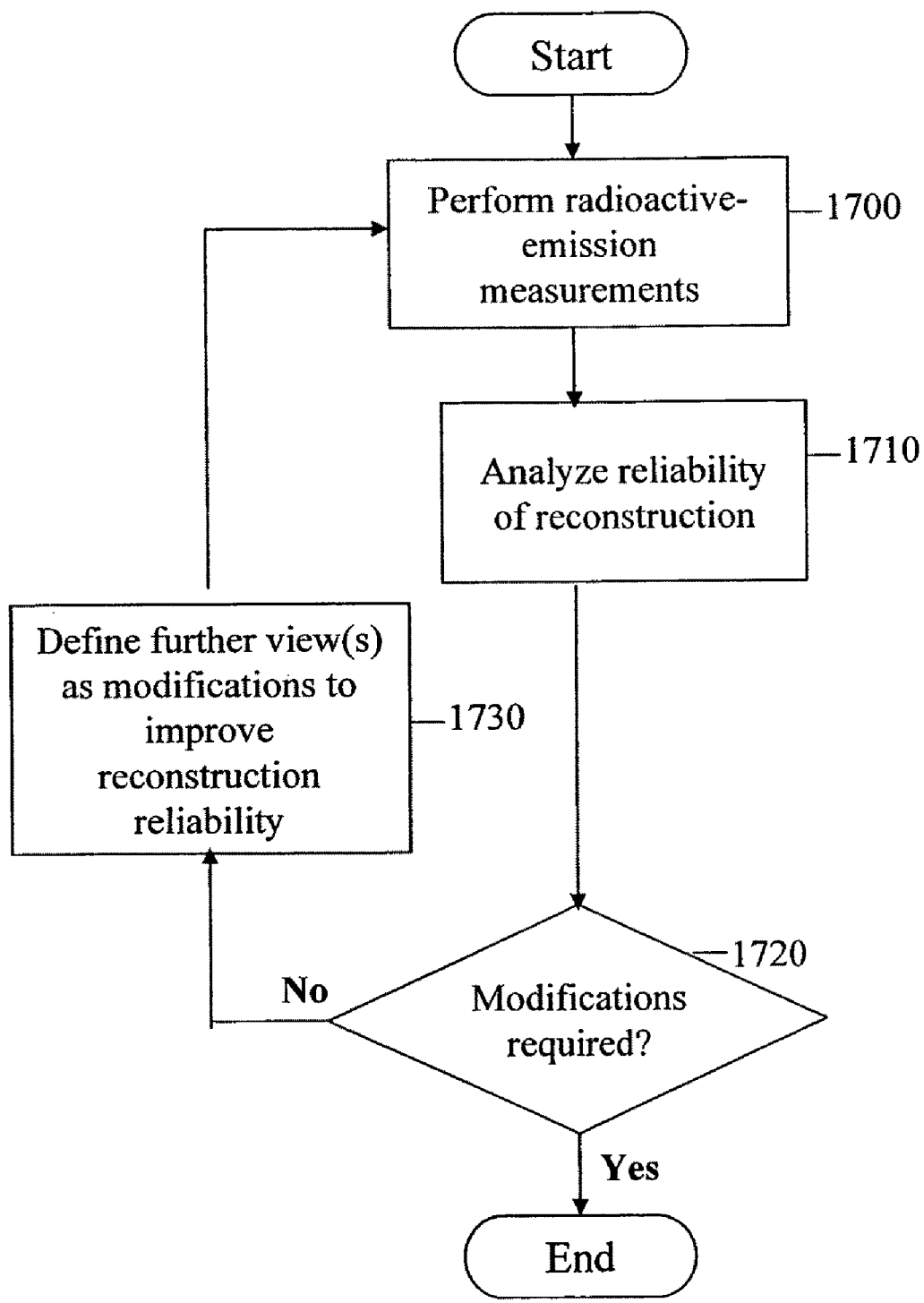
FIG. 17 is a simplified flowchart of method for stabilizing the reconstruction of an imaged volume with dynamic view definition, according to a preferred embodiment of the present invention.

The active vision embodiments discussed above may be provided as modifications to improve reconstruction reliability. Reference is now made to FIG. 17, which is a simplified flowchart of a method for stabilizing the reconstruction of an imaged volume with dynamic view definition, according to a preferred embodiment of the present invention. FIG. 17 presents an embodiment in which the modifications to improve reconstruction reliability are performed by the active vision techniques described herein. In step 1700 radioactive emission measurements are performed. In step 1710, the reliability of reconstruction is analyzed, for example utilizing the SVD analysis described above. In step 1720, a determination is made whether measurements are finished, preferably based on the reliability analysis performed in step 1710. If it is determined that modifications are required, further views are defined without ceasing the measurement process, and preferably utilizing active vision techniques. Further measurements are then performed at the newly-defined views, until an adequate reconstruction reliability is achieved or it is decided to terminate the measurement process for other reasons.

The above-described improved reconstruction reliability and active vision techniques enable high-quality reconstruction based on data collected from a limited collection of views. The ability to improve reconstruction reliability, both before and during imaging, reduces the need for repeated imaging to obtain additional measurements. Reconstructing the intensity distribution from a smaller quantity of collected data utilizing a stable reconstruction process simplifies the computational process. Furthermore, these methods enable resolving the current conflict between the relatively large-pixel detectors needed for measurement speed and data processing considerations, with the small-pixel detectors needed until now to obtain a high-resolution reconstruction. The abovedescribed embodiments are particularly suitable for medical imaging purposes, where a high-resolution image is needed and it is desired to minimize the difficulties of the patient undergoing the diagnostic testing or treatment.

This application claims the benefit of:
International Application PCT/IL2005/001215, filed Nov. 16, 2005;
International Application PCT/IL2005/001173, filed Nov. 9, 2005,
U.S. Application 60/700,318, filed Jul. 19, 2005;
U.S. Application 60/700,299, filed Jul. 19, 2005;
U.S. Application 60/700,317, filed Jul. 19, 2005;
U.S. Application 60/700,753, filed Jul. 20, 2005;
U.S. Application 60/700,752, filed Jul. 20, 2005;
U.S. Application 60/702,979, filed Jul. 28, 2005;
U.S. Application 60/720,034, filed Sep. 26, 2005;
U.S. Application 60/720,652, filed Sep. 27, 2005;
U.S. Application 60/720,541, filed Sep. 27, 2005,
U.S. Application 60/750,287, filed Dec. 13, 2005;

U.S. Application 60/750,334, filed Dec. 15, 2005;
U.S. Application 60/750,597, filed Dec. 15, 2005;
U.S. Application 60/800,845, filed May 17, 2006;
U.S. Application 60/800,846, filed May 17, 2006;
Israel Application 171346, filed Oct. 10, 2005;
Israel Application 172349, filed Nov. 27, 2005;
U.S. Application 60/741,440, filed Dec. 2, 2005;
International Application PCT/IL2006/000059, filed Jan. 15, 2006;
U.S. Application 60/763,458, filed Jan. 31, 2006;
International Application PCT/IL2006/000562, filed May 11, 2006;
U.S. Application 60/799,688, filed May 11, 2006; and
U.S. Application 60/816,970, filed Jun. 28, 2006.
Information of all of which is herein incorporated in entirety by reference.

This application further incorporates by reference all the information of the International Application entitled "Imaging Protocols" which is being co-filed by the same assignee of the present invention on Jul. 19, 2006.

It is expected that during the life of this patent many relevant detection probes, detector types, radiation-based detection systems, algorithms for reconstruction and analyzing the reliability of reconstruction, and algorithms will be developed and the scope of the corresponding terms are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for stabilizing the reconstruction of an imaged volume, comprising:
    performing an analysis of the reliability of reconstruction of a radioactive-emission density distribution of said volume from radiation detected over a specified set of views; and
    defining modifications to at least one of a reconstruction process and a data collection process to improve said reliability of reconstruction, in accordance with said analysis.

2. A method according to claim 1, further comprising calculating a measure of said reliability of reconstruction, said measure of reliability of reconstruction being for determining a necessity of performing said modifications.

3. A method according to claim 1, further comprising:
    providing a detection probability matrix defining a respective detection probability distribution of said volume for each of said views; calculating the singular values of said detection probability matrix;
    identifying singular values as destabilizing singular values.

4. A method according to claim 3, further comprising performing singular value decomposition (SVD) of said probability matrix.

5. A method according to claim 3, wherein said identifying comprises:
    for each of said singular values, calculating a respective ratio of said singular value to a largest singular value; and
    specifying a singular value having a respective ratio below a specified threshold as destabilizing.

6. A method according to claim 3, further comprising calculating a condition number of said probability matrix as a measure of said reliability of reconstruction.

7. A method according to claim 6, further comprising performing said identifying if said condition number exceeds a specified magnitude.

8. A method according to claim 3, wherein said modification comprises defining constraints on said reconstruction process to reduce an effect of said destabilizing singular values upon a reconstruction of said volume.

9. A method according to claim 3, further comprising identifying, for a destabilizing singular value, an associated unreliable voxel of said reconstructed volume.

10. A method according to claim 3, further comprising identifying, for a destabilizing singular value, an associated unreliable linear combination of voxels of a reconstruction of said volume.

11. A method according to claim 1, wherein said modification comprises smoothing a selected portion of said volume during said reconstruction.

12. A method according to claim 1, wherein said modification comprises uniting multiple voxels of said volume into a single element of said reconstruction.

13. A method according to claim 1, wherein said modification comprises defining views for imaging said volume.

14. A method according to claim 13, wherein said defining is performed to obtain a required resolution.

15. A method according to claim 13, wherein said defining comprises specifying multiple scan densities for imaging said volume.

16. A method according to claim 15, wherein each of said scan densities is for a different respective portion of said volume.

17. A method according to claim 13, wherein said defining is performed dynamically during radioactive-emission measurements of said volume.

18. A method according to claim 13, further comprising performing radioactive-emission measurements of the body structure, at a predetermined set of views;
    and wherein said modification comprises dynamically-defined views for continued imaging of said volume.

19. A method according to claim 9, wherein said modification comprises defining a non-uniform scan for data collection.

20. The method of claim 1, further comprising providing at least one intensity distribution, wherein an intensity distribution comprises a representation of a radioactive-emission density distribution of said volume.

* * * * *